US010907145B2

(12) United States Patent
Rege et al.

(10) Patent No.: US 10,907,145 B2
(45) Date of Patent: Feb. 2, 2021

(54) CHEMOTHERAPEUTIC DRUG-CONJUGATED RESINS AND THEIR PREFERENTIAL BINDING OF METHYLATED DNA

(71) Applicant: ARIZONA BOARD OF REGENTS ON BEHALF OF ARIZONA STATE UNIVERSITY, Scottsdale, AZ (US)

(72) Inventors: Kaushal Rege, Chandler, AZ (US); Kevin Lin, Gilbert, AZ (US); Sudhakar Godeshala, Tempe, AZ (US); Taraka Sai Pavan Grandhi, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/915,909

(22) Filed: Mar. 8, 2018

(65) Prior Publication Data
US 2018/0258416 A1    Sep. 13, 2018

Related U.S. Application Data

(60) Provisional application No. 62/468,729, filed on Mar. 8, 2017.

(51) Int. Cl.
  *C12N 15/10* (2006.01)
  *B01D 15/38* (2006.01)
  *B01J 20/291* (2006.01)

(52) U.S. Cl.
  CPC ....... *C12N 15/101* (2013.01); *B01D 15/3804* (2013.01); *B01J 20/291* (2013.01); *B01J 2220/80* (2013.01)

(58) Field of Classification Search
  CPC .. C12N 15/101; B01D 15/3804; B01J 20/291; B01J 2220/80
  USPC ....................................... 536/25.4
  See application file for complete search history.

(56) References Cited

U.S. PATENT DOCUMENTS

| 4,024,224 | A  | * | 5/1977  | Arcamone | C07H 15/252 514/34 |
|-----------|----|---|---------|----------|---------------------|
| 9,801,954 | B2 |   | 10/2017 | Rege     |                     |
| 9,856,332 | B2 | * | 1/2018  | Rege     | A61L 27/18          |
| 10,232,345| B2 |   | 3/2019  | Rege     |                     |
| 2012/0196923 | A1 | | 8/2012  | Rege     |                     |

FOREIGN PATENT DOCUMENTS

| WO |    2010132876 |   | 11/2010 |
|----|---------------|---|---------|
| WO |    2013055971 |   | 4/2013  |
| WO | WO 2015/034925 | * | 3/2015  |
| WO |    2015069694 |   | 5/2016  |
| WO |    2016130928 |   | 8/2016  |

OTHER PUBLICATIONS

Kangaspeska et al. Transient cyclical methylation of promoter DNA. Nature vol. 452|6, p. 112-116, Mar. 2008. (Year: 2008).*
Arcamone et al. Synthesis and Biological Evaluation of Some 14-O-Acyl Derivatives of Adriamycin. Journal of Medicinal Chemistry, 1974, vol. 17, No. 3, p. 335-337. (Year: 1974).*
Tong et al. Ring-Opening Polymerization Mediated Chemo- and Regioselective Conjugation of Doxorubicin to Polylactide. Polymer Preprints 50(1), 320, 2009. (Year: 2009).*
Allamane S, et al. Bacterial DNA methylation and gene transfer efficiency. Biochemical and biophysical research communications. 2000;276(3):1261-4.
Al-Sukhun S, et al. Current understanding of the biology of advanced bladder cancer. Cancer. 2003;97(S8):2064-75.
Alton, E., et al., Non-invasive liposome-mediated gene delivery can correct the ion transport defect in cystic fibrosis mutant mice. Nature genetics 1993, 5, 135-142.
Andersson E, et al. Size-based enrichment of exfoliated tumor cells in urine increases the sensitivity for DNA-bases detection of bladder cancer. PloS one. 2014;9(4):e94023.
Arya, D. P. ,et al., Aminoglycoside—Nucleic Acid Interactions: Remarkable Stabilization of DNA and RNA Triple Helices by Neomycin. Journal of the American Chemical Society 2001, 123, 5385-5395.
Bailly C, et al. DNA recognition by two mitoxantrone analogues: Influence of the hydroxyl groups. FEBS Letters. 1996;379(3):269-72. doi: http://dx.doi.org/10.1016/0014-5793(95)01528-0.
Banerjee, R., et al, Plasmid DNA-Mediated Gene Therapy. Burger's Medicinal Chemistry and Drug Discovery 2003.
Barras, F., et al., The great GATC: DNA methylation in *E. coli*. Trends in Genetics 1989, 5, 139-143.
Bernert H. Promoter Hypermethylation of Candidate Tumor Suppressor Genes in Urinary Bladder and Prostate Cancer: Citeseer; 2009.
Bird, A., DNA methylation patterns and epigenetic memory. Genes & development 2002, 16, 6-21.
Bottom, C. B., et al., Mechanism of the ninhydrin reaction. Biochemistry and Molecular Biology Education 1978, 6, 4-5.
Brena, R. M., et al., Quantitative assessment of DNA methylation: potential applications for disease diagnosis, classification, and prognosis in clinical settings. Journal of molecular medicine 2006, 84, 365-377.

(Continued)

*Primary Examiner* — Yin-Horng Shiao
(74) *Attorney, Agent, or Firm* — Quarles & Brady LLP

(57) ABSTRACT

Ligands and methods for selectively binding hypermethylated DNA from a sample. The ligands include a CG-region binding molecule-conjugated resin derived from the aminoglycoside antibiotic amikacin. Furthermore, the CG-region binding molecule may be conjugated to the resin with a crosslinker and/or may be modified with one or more of long chain and short chain alkyl, aryl, piperazinyl, piperidyl, and pyrrolidyl groups. Such ligands are used in methods for contacting a sample to thereby selectively bind hypermethylated DNA.

21 Claims, 13 Drawing Sheets

(56) References Cited

OTHER PUBLICATIONS

Caramelo-Nunes, C., et al., Specific berenil-DNA interactions: An approach for separation of plasmid isoforms by pseudo-affinity chromatography. Analytical biochemistry 2011, 412, 153-158.

Casadesús, J., et al., Epigenetic gene regulation in the bacterial world. Microbiology and molecular biology reviews 2006, 70, 830-856.

Chan MW, et al. Hypermethylation of multiple genes in tumor tissues and voided urine in urinary bladder cancer patients. Clinical Cancer Research. 2002;8(2):464-70.

Chang, C.-S., et al., Preparation of inorganic-organic anion-exchange membranes and their application in plasmid DNA and RNA separation. Journal of Membrane Science 2008, 311, 336-348.

Chen, X., Modeling of experimental adsorption isotherm data. Information 2015, 6, 14-22.

Chung W, et al. Detection of bladder cancer using novel DNA methylation biomarkers in urine sediments. Cancer Epidemiology Biomarkers & Prevention. 2011;20(7):1483-91.

Cortesi, R., et al., Delivery systems for DNA-binding drugs as gene expression modulators. Drug discovery today 2001, 6, 893-904.

Cross, D., et al., Gene therapy for cancer treatment: past, present and future. Clinical medicine & research 2006, 4, 218-227.

De Carvalho DD, et al. DNA methylation screening identifies driver epigenetic events of cancer cell survival. Cancer cell. 2012;21(5):655-67.

Delpu, Y., et al., DNA methylation and cancer diagnosis. International journal of molecular sciences 2013, 14, 15029-15058.

Denny WA, et al. Kinetics of the binding of mitoxantrone, ametantrone and analogues to DNA: relationship with binding mode and antitumour activity. Anticancer Drug Des. 1990;5(2):189-200. PubMed PMID: 2357264.

Dinh, N. P., et al., Probing the interaction mode in hydrophilic interaction chromatography. Journal of Chromatography A 2011, 1218, 5880-5891.

Esteller M, et al. Detection of aberrant promoter hypermethylation of tumor suppressor genes in serum DNA from non-small cell lung cancer patients. Cancer research. 1999;59(1):67-70.

Ferreira, S., et al., Affinity analysis and application of dipeptides derived from l-tyrosine in plasmid purification. Journal of Chromatography B 2015, 1006, 47-58.

Foo, K., et al., Insights into the modeling of adsorption isotherm systems. Chemical engineering journal 2010, 156, 2-10.

Goessl C, et al. DNA-based detection of prostate cancer in blood, urine, and ejaculates. Annals of the New york Academy of sciences. 2001;945(1):51-8.

Grandhi TS, et al. Sensitizing cancer cells to TRAIL-induced death by micellar delivery of mitoxantrone. Nanomedicine (Lond). 2014;9(12):1775-88. doi: 10.2217/nnm.13.125. PubMed PMID: 24195660.

Grandhi, et al. "Aminoglycoside antibiotic-derived anion-exchange microbeads for plasmid DNA binding and in situ DNA capture". ACS applied materials & interfaces 6.21 (2014): 18577-18589.

Heyn, H., et al., DNA methylation profiling in the clinic: applications and challenges. Nature reviews. Genetics 2012, 13, 679.

Hoque MO, et al. Quantitation of promoter methylation of multiple genes in urine DNA and bladder cancer detection. Journal of the National Cancer Institute. 2006;98(14):996-1004.

NCBI GenBank EU921840.1 SYN Aug. 28, 2008—accessed online at https://www.ncbi.nlm.nih.gov/nuccore/EU921840.

Huang, H.-C., et al., Simultaneous enhancement of photothermal stability and gene delivery efficacy of gold nanorods using polyelectrolytes. Acs Nano 2009, 3, 2941-2952.

Kadonaga, J. T., et al., Affinity purification of sequence-specific DNA binding proteins. Proceedings of the National Academy of Sciences 1986, 83, 5889-5893.

Kaufman DS, et al. Bladder cancer. The Lancet. 2009;374(9685):239-49.

Kaur P, et al. Hydrophobicity of methylated DNA as a possible mechanism for gene silencing. Physical biology. 2012;9(6):065001.

Kim J, et al. A programmable microfluidic cell array for combinatorial drug screening. Lab on a chip. 2012;12(10):1813-22. doi: 10.1039/c2lc21202a. PubMed PMID: 22456798.

Kim YK, et al. Epigenetic markers as promising prognosticators for bladder cancer. Int J Urol. 2009;16(1):17-22. doi: 10.1111/j.1442-2042.2008.02143.x. PubMed PMID: 18721202.

Kizek, R., et al., Anthracyclines and ellipticines as DNA-damaging anticancer drugs: recent advances. Pharmacology & therapeutics 2012, 133, 26-39.

Krassenstein R, et al. Detection of breast cancer in nipple aspirate fluid by CpG island hypermethylation. Clinical Cancer Research. 2004;10(1):28-32.

Kurth K, et al. Factors affecting recurrence and progression in superficial bladder tumours. European Journal of Cancer. 1995;31(11):1840-6.

Larré S, et al. Screening for bladder cancer: rationale, limitations, whom to target, and perspectives. European urology. 2013;63(6):1049-58.

Li Y, et al. Hypermethylation in gastric cancer. Clinica Chimica Acta. 2015;448:124-32. doi: http://dx.doi.org/10.1016/j.cca.2015.07.001.

Liu, Q.-S., et al., Adsorption isotherm, kinetic and mechanism studies of some substituted phenols on activated carbon fibers. Chemical Engineering Journal 2010, 157, 348-356.

Lobner-Olesen, A., et al, Dam methylation: coordinating cellular processes. Current opinion in microbiology 2005, 8, 154-160.

Lund, L. N., et al., Novel peptide ligand with high binding capacity for antibody purification. Journal of Chromatography a 2012, 1225, 158-167.

Mannhold, R., et al., Calculation of molecular lipophilicity: State-of-the-art and comparison of log P methods on more than 96,000 compounds. Journal of pharmaceutical sciences 2009, 98, 861-893.

McCaffrey JA, et al. Phase II trial of docetaxel in patients with advanced or metastatic transitional-cell carcinoma. Journal of Clinical Oncology. 1997;15(5):1853-7.

Miryala B, et al. Aminoglycoside-derived amphiphilic nanoparticles for molecular delivery. Colloids and Surfaces B: Biointerfaces. 2016;146:924-37. doi: http://dx.doi.org/10.1016/j.colsurfb.2016.06.028.

Nelson, D. L., Lehninger, A. L., Cox, M. M., Lehninger principles of biochemistry, Macmillan 2008.

Nobs, L., et al., Current methods for attaching targeting ligands to liposomes and nanoparticles. Journal of Pharmaceutical sciences 2004, 93, 1980-1992.

Ochoa, J.-L., Hydrophobic (interaction) chromatography. Biochimie 1978, 60, 1-15.

Park, J. S., et al., Desorption of single-stranded nucleic acids from graphene oxide by disruption of hydrogen bonding. Analyst 2013, 138, 1745-1749.

Parker BS, et al. A Molecular Understanding of Mitoxantrone-DNA Adduct Formation Effect of Cytosine Methylation and Flanking Sequences. Journal of Biological Chemistry. 2004;279(18):18814-23.

Parker BS, et al. Mitoxantrone Mediates Demethylation and Re-Expression of Cyclin D2, Estrogen Receptor 14.3. 3 Sigma in Breast Cancer Cells. Cancer biology & therapy. 2003;2(3):259-63.

Peetla, C., et al., Drug resistance in breast cancer cells: biophysical characterization of and doxorubicin interactions with membrane lipids. Molecular pharmaceutics 2010, 7, 2334-2348.

Pereira, L. R., et al., Hydrophobic interaction membrane chromatography for plasmid DNA purification: Design and optimization. Journal of separation science 2010, 33, 1175-1184.

Pe'rez-Arnaiz, C., et al., New insights into the mechanism of the DNA/doxorubicin interaction. The Journal of Physical Chemistry B 2014, 118, 1288-1295.

Qureshi SA, et al. Utility of DNA methylation markers for diagnosing cancer. International Journal of Surgery. 2010;8(3):194-8.

Rafferty, J. L., et al., Mobile phase effects in reversed-phase liquid chromatography: A comparison of acetonitrile/water and methanol/water solvents as studied by molecular simulation. Journal of Chromatography A 2011, 1218, 2203-2213.

(56) References Cited

OTHER PUBLICATIONS

Reinert T. Methylation markers for urine-based detection of bladder cancer: the next generation of urinary markers for diagnosis and surveillance of bladder cancer. Advances in urology. 2012;2012.

Ringquist, S., et al., The *Escherichia coli* chromosome contains specific, unmethylated dam and dcm sites. Proceedings of the National Academy of Sciences 1992, 89, 4539-4543.

Robertson KD. DNA methylation and human disease. Nature Reviews Genetics. 2005;6(8):597-610.

Shakil, S., et al., Aminoglycosides versus bacteria—a description of the action, resistance mechanism, and nosocomial battleground. Journal of biomedical science 2008, 15, 5-14.

Siegel RL, et al. Cancer statistics, 2016. CA: a cancer journal for clinicians. 2016;66(1):7-30.

Sousa, F., et al., Affinity chromatography approaches to overcome the challenges of purifying plasmid DNA. Trends in biotechnology 2008, 26, 518-525.

Sousa, F., et al., Improvement of transfection efficiency by using supercoiled plasmid DNA purified with arginine affinity chromatography. The journal of gene medicine 2009, 11, 79-88.

Stadler, J., et al., Plasmid DNA purification. The journal of gene medicine 2004, 6.

Su S-F, et al. A panel of three markers hyper-and hypomethylated in urine sediments accurately predicts bladder cancer recurrence. Clinical Cancer Research. 2014;20(7):1978-89.

Tacar, O., et al., Doxorubicin: an update on anticancer molecular action, toxicity and novel drug delivery systems. Journal of Pharmacy and Pharmacology 2013, 65, 157-170.

Takae, S., et al., Ligand density effect on biorecognition by PEGylated gold nanoparticles: regulated interaction of RCA120 lectin with lactose installed to the distal end of tethered PEG strands on gold surface. Biomacromolecules 2005, 6, 818-824.

Taylor DJ, et al. Parallel screening of FDA-approved antineoplastic drugs for identifying sensitizers of TRAIL-induced apoptosis in cancer cells. BMC cancer. 2011;11:470. doi: 10.1186/1471-2407-11-470. PubMed PMID: 22044796; PMCID: PMC3223153.

Tseng, W.-C., et al., Effect of alcohol on purification of plasmid DNA using ion-exchange membrane. Journal of membrane science 2004, 233, 161-167.

Tsou, J. A., et al., DNA methylation analysis: a powerful new tool for lung cancer diagnosis. Oncogene 2002, 21, 5450.

Tuszynski, M. H., et al., A phase 1 clinical trial of nerve growth factor gene therapy for Alzheimer disease. Nature medicine 2005, 11, 551.

Vanyushin, B., Enzymatic DNA methylation is an epigenetic control for genetic functions of the cell. Biochemistry (Moscow) 2005, 70, 488-499.

Venables, D. S., et al., Spectroscopy and dynamics of mixtures of water with acetone, acetonitrile, and methanol. The Journal of Chemical Physics 2000, 113, 11222-11236.

Wang Y, et al. An epigenetic biomarker combination of PCDH17 and POU4F2 detects bladder cancer accurately by methylation analyses of urine sediment DNA in Han Chinese. Oncotarget. 2016;7(3):2754-64. doi: 10.18632/oncotarget.6666. PubMed PMID: 26700620; PMCID: PMC4823069.

Weiss C, et al. Radiochemotherapy with cisplatin and 5-fluorouracil after transurethral surgery in patients with bladder cancer. International Journal of Radiation Oncology* Biology* Physics. 2007;68(4):1072-80.

Wolff EM, et al. Unique DNA methylation patterns distinguish noninvasive and invasive urothelial cancers and establish an epigenetic field defect in premalignant tissue. Cancer research. 2010;70(20):8169-78.

Wong, S. S., Chemistry of protein conjugation and cross-linking, CRC press 1991.

Xiu, L., et al., Effective protein separation by coupling hydrophobic interaction and reverse phase chromatography for top-down proteomics. Analytical chemistry 2014, 86, 7899-7906.

Yafi F, et al. First-and second-line therapy for metastatic urothelial carcinoma of the bladder. Current Oncology. 2011;18(1):25-34.

Yang F, et al. Doxorubicin, DNA torsion, and chromatin dynamics. Biochimica et Biophysica Acta (BBA)—Reviews on Cancer. 2014;1845(1):84-9. doi: http://dx.doi.org/10.1016/j.bbcan.2013.12.002.

Yegnasubramanian, S., et al., DNA hypomethylation arises later in prostate cancer progression than CpG island hypermethylation and contributes to metastatic tumor heterogeneity. Cancer research 2008, 68, 8954-8967.

Yemm, E., et al, The determination of amino-acids with ninhydrin. Analyst 1955, 80, 209-214.

Zingg, J.-M., et al., Genetic and epigenetic aspects of DNA methylation on genome expression, evolution, mutation and carcinogenesis. Carcinogenesis 1997, 18, 869-882.

\* cited by examiner

DOXORUBICIN-CONJUGATED AMIKABEADS (DOXO-BEADS)

Fig. 4A
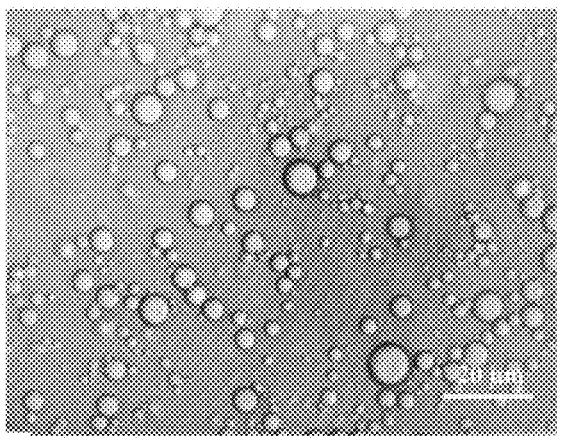
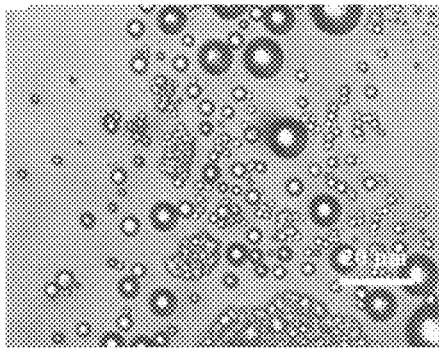
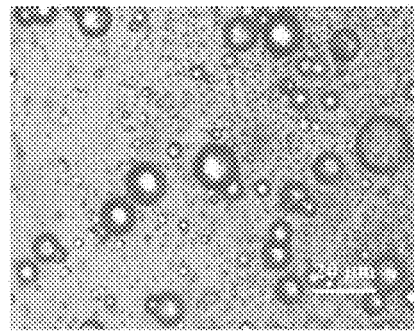
Fig. 4B
Fig. 4C

Fig. 6A
Fig. 6B
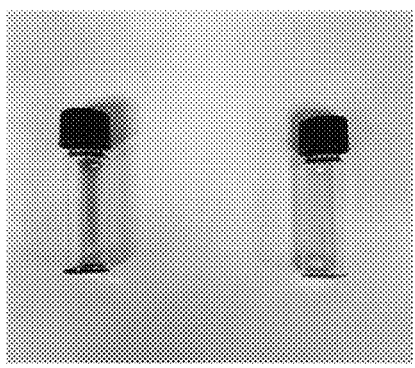
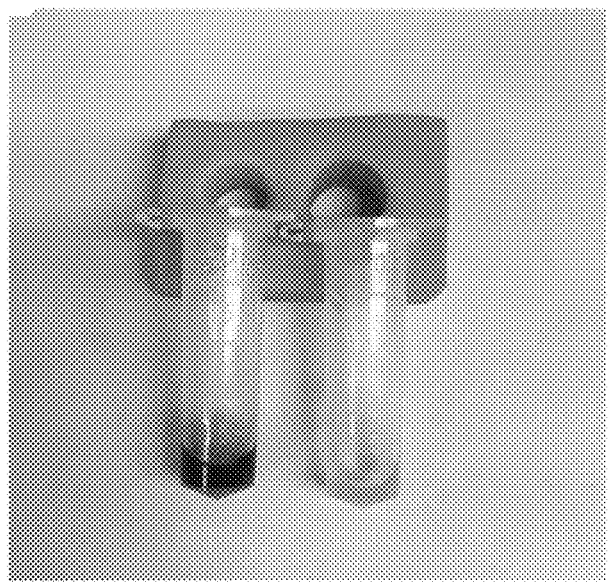
Fig. 6C

CHEMOTHERAPEUTIC DRUG-CONJUGATED RESINS AND THEIR PREFERENTIAL BINDING OF METHYLATED DNA

CROSS-REFERENCE TO RELATED APPLICATIONS

This application is based on, claims a priority benefit from, and incorporates herein by reference, U.S. Provisional Patent Application No. 62/468,729, filed Mar. 8, 2017, and entitled "Novel Methylation Specific DNA Binding Ligands and Methods."

GOVERNMENT FUNDING STATEMENT

This invention was made with government support under R01 GM093229 awarded by the National Institutes of Health, and 1067840 awarded by the National Science Foundation. The government has certain rights in the invention

FIELD OF TECHNOLOGY

This disclosure relates to DNA binding molecules that are conjugated to aminoglycoside amikacin hydrogel resins (such as microbeads) for methylated DNA binding.

BACKGROUND

Cancer is one of the biggest challenges facing the present healthcare community. Due to limited reduction in the mortality rates over the past years, cancer is soon projected to overtake cardiac related diseases in the rate of growth. The cost of treatments are expected to spiral to $157 billion by 2020 (cancer.gov/news-events/press-releases/2011/Cost-Cancer2020). Cancer diagnostics play a very important role in detecting the onset of disease and allowing for continuous monitoring of the disease for patients in remission. Earlier detection of primary cancer onset or secondary recurrence can significantly increase the chances of patient survival and late stage detection of the disease is almost certainly deadly. In short, the earlier the detection of the disease, the better the chance of a cure.

However, there is a clear dearth of easy to use, fast, inexpensive, reproducible diagnostic devices and methods that can accurately detect the onset and progression of the cancer disease. Novel cancer detection devices, membranes and resins can greatly benefit patients for daily monitoring of the disease, and also allow for cancer screening in remote areas of the world without access to advanced diagnostic technologies. For example, delivery of plasmid DNA (pDNA) is being studied in gene therapy for cancer, AIDS, cystic fibrosis, Parkinson's disease and Alzheimer's disease.

At the laboratory scale, plasmids are typically processed in *E. coli*, purified using kits, and delivered to mammalian cells using viral or non-viral carriers. The strain of *E. coli* employed in these processes not only influences the pDNA's yield, but also its methylation status, which is governed by specific enzymes present in the bacteria that manage epigenetic modifications in the plasmid. These epigenetic modifications on plasmid DNA ultimately determine the efficacy of transgene expression in mammalian cells.

Purification of plasmid DNA is an important first step in developing a cancer detection device, Different models including anion-exchange chromatography, affinity/pseudo-affinity chromatograph, hydrophobic interaction chromatography (HIC), and size-exclusion chromatography have been used for the purification of pDNA. In addition, membrane-based approaches have also been investigated for purifying DNA. Affinity chromatography approaches exploit selective biomolecular interactions between plasmid DNA molecules and surface-immobilized affinity or pseudo-affinity ligands for purification of pDNA from culture broths. Ligands, including arginine, histidine, berenil, zinc fingers, LacI-LacZ moieties and triple-helix forming nucleotide sequences, have been studied for purifying plasmid DNA using affinity chromatography. The yield and purity of pDNA depends on the efficacy of the pseudo-affinity ligands employed, which may not possess high affinities for DNA. Epigenetic modifications on pDNA influences interactions with the immobilized affinity ligands, which in turn, also affects the efficacy of binding and purification. Further, these ligands have low stabilities and are expensive to use. Therefore, it is imperative to design and develop new plasmid DNA binding materials that can eliminate or at least minimize the above identified problems.

SUMMARY

Embodiments herein relate to compositions for selectively binding methylated DNA, comprising a CG-region binding molecule-conjugated resin, wherein the CG-region binding molecule is conjugated to the resin with a cross linker. In certain embodiments, the resin is aminoglycoside-derived microbeads, having a structure of formula 1:

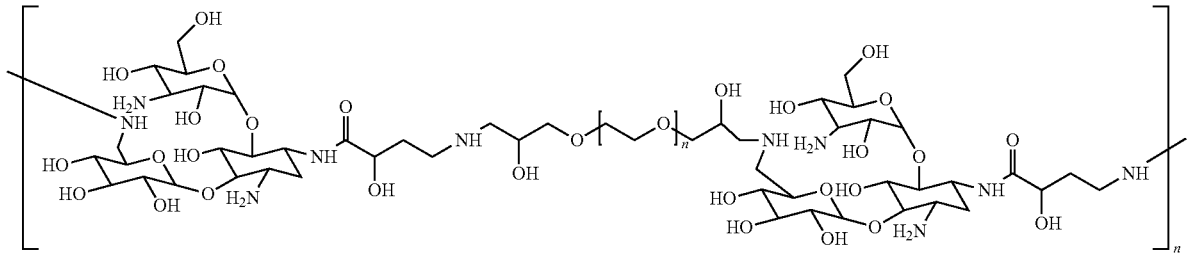

In certain embodiments, the CG-region binding molecule is selected from the group consisting of Doxorubicin, Mitoxantrone, Daunomycin, Amonafide, Etoposide, Adenine, Guanine, Cyclosporamide, Vincristine, Netropsin, Furamidines, Ethidium bromide, Proflavine, Epirubicin, 8-Aminoacridine, Mitomycin, Distamycin, Idarubicin, Valrubicin, Pixantrone, Bleomycin, Methotrexate, and Berenil. In some embodiments, the CG-region binding molecule is Doxorubicin. In other embodiments, the CG-region binding molecule is Berenil.

Further, embodiments of the technology describe methods for selectively binding methylated DNA. In certain embodiments, the method comprises contacting a sample containing methylated DNA with a CG-region binding molecule-conjugated resin, wherein said CG-region binding molecule is conjugated to the resin with a crosslinker.

Hypermethylation of the CpG islands significantly increases the local hydrophobicity of the DNA, which can be exploited towards developing novel hypermethylation specific DNA intercalating drugs and resins than can isolate them.

BRIEF DESCRIPTION OF THE DRAWINGS

FIGS. 4A-C: Observations of unmodified Amikabeads (A), doxo-beads (B) and berenil-beads (C). Aggregation was shown in the doxo-beads and berenil-beads. The aggregation was due to the conjugation process between 1,4-CHDDE and unmodified Amikabeads.

FIGS. 6A-C: Verifications of doxo-beads and berenil-beads generation by visualization and ninhydrin assay. (A) Doxo-beads (red solution) and berenil-beads (yellow solution) were dissolved in the DMSO solvent showing two distinguished colors. (B) The dark red (doxo-beads) and yellow (berenil-beads) pellets were left in the tubes after removing excess free drug in the supernatant. (C) The ninhydrin assay was performed on doxo-beads (right tube) and unmodified Amikabeads (left tube). The bluish-purple color in the left tube indicated the presence of primary amine group on unmodified Amikabeads while the light yellow color in the right tube represented the absence of primary amine group on doxo-beads and proved the generation process was successfully.

DETAILED DESCRIPTION

Figure 1A:
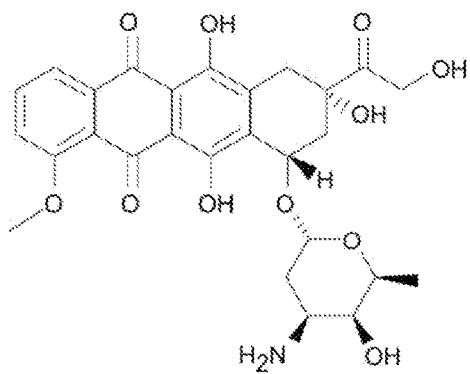
FIGS. 1A-B: Schematics of anticancer drugs, (A) doxorubicin and (B) berenil, employed in the research scheme.

This technology disclosed herein is described in one or more exemplary embodiments in the following description with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein A novel resin material composed of small molecule ligands that utilize mixed mode interactions and bind to hypermethylated cancer genomic DNA is described herein. Hypermethylated DNA is a key emerging biomarker in several diseases including cancer. Further, hypermethylation of CpG islands is known to be a powerful epigenetic mechanism for gene silencing. Cancer cells often hypermethylate CpG islands in the promoter regions of multiple anti-cancer and tumor supressor genes to silence said genes, thus making the hypermethylation status of CpG islands very important for cancer detection.

Currently, no small-molecule ligands are available for the purification/detection/enrichment of the hypermethylated DNA species. Some existing approaches use expensive methyl binding proteins or antibody-binding ligands coated on resins for purification/isolation. To avoid using expansive antibody or methyl binding proteins to bind the hypermethylated DNA regions, the current technology presents an antibody free, small molecule resin-based, inexpensive system. In certain embodiments, the usage of novel, modified anticancer chemotherapeutics conjugated resins that can selectively bind hypermethylated DNA specific to cancerous cells are disclosed herein.

We previously developed novel aminoglycoside based microbead and macroporous gel resins for plasmid DNA binding and purification. These resins are composed of a crosslinked aminoglycoside backbone that offers abundant amino and hydroxyl rich sites for conjugating biomolecule specific ligands for binding, purification and other interactions.

We hypothesized that DNA intercalating anticancer chemotherapeutic drugs such as doxorubicin and mitoxantrone could be exploited as novel small molecule agents for cancer specific DNA binding and purification towards novel cancer diagnostics. Conjugating multiple units of doxorubicin on the surface of aminoglycoside microbead and macroporous resins could allow for their usage for multiple nucleic acid applications. We developed novel chemistries in order to successfully conjugate anthracycline and anthracenedione drugs such as doxorubicin, mitoxantrone to the Amikabeads. Here, we propose a broad and useful extension of the chemotherapeutic drug conjugated resins towards their application into novel cancer specific DNA binding and detection. Our technology utilizes the ability of drugs such as doxorubicin to bind the CG rich region of cancer cells towards detection of cancer cell specific hypermethylated DNA segments.

One of the embodiments of the resins would include an anticancer chemotherapeutics based hypermethylated DNA specific ligands that can bind and detect the presence of cancer cells. As mentioned before, hypermethylation of CG islands in the tumor suppressor gene promoter regions cause epigenetic silencing and subsequent progression of the disease. This represents an important adaptation in multiple cancer types. We hypothesized that CG binding drugs such as doxorubicin are strong leads for synthesis of subsequent generations of selective ligands for enriching hypermethylated DNA from disease (e.g. cancer) cells. Anthracycline (e.g. doxorubicin) and anthracenedione (e.g. mitoxantrone) drugs exert their anti-cancer activity by binding DNA, with preferential binding to CG rich sites. These CG rich sites also are the sites for hypermethylation. As mentioned before, our technology utilizes the natural ability of drugs such as doxorubicin to bind the CG rich region of cancer cells towards detection of cancer cell specific CpG hypermethylated DNA segments.

Ligand embodiments can include novel additions to existing chemotherapeutics to exploit mixed mode interactions between the DNA and the resin to selectively capture the hypermethylated DNA. For example, in one embodiment, the hydroxyl groups of doxorubicin drug could be modified with 2-5 carbon alkyl chains, aromatic groups to increase the overall hydrophobicity of the resin. Increased hydrophobicity of the resin would allow selective binding to hypermethylated DNA. We hypothesize that the hypermethylated DNA sections will be more hydrophobic compared to the methylated and non-methylated sections of the genome and hence will likely differentially interact with modified ligands. Ligands that can distinguish cancer specific hypermethylated DNA from the non-hypermethylated DNA can allow for their detection and allow for sensitive cancer specific diagnostics.

Commercially available resins to bind hypermethylated DNA comprise of resins conjugated with methylation specific antibodies or DNA methyl transferase proteins which make them very expensive to use. Our resins are the first of its kind to utilize novel modified small molecule chemotherapeutic ligands that can selectively bind cancer specific hypermethylated DNA.

Non-Limiting Examples

Materials

Amikacin hydrate and poly(ethylene glycol) diglycidyl ether (PEGDE) were purchased from Sigma-Aldrich Inc. (St. Louis, Mo.). Silicone oil and mineral oil were purchased from Acros Organics (Pittsburgh, Pa.). Span 80 as the surfactant agent was purchased from TCI America (Portland, Oreg.). Nanopure water was utilized for the preparation of Amikabeads. BD Precision Glide needles and syringes were purchased from Becton, Dickinson and Company (Franklin Lakes, N.J.). Cell culture media and 10,000 units/mL penicillin were purchased from Hyclone (Logan, Utah). Qiagen Giga kit (pDNA extraction kits) was purchased from Qiagen Inc. (Alameda, Calif.). Doxorubicin and berenil as the highly selective ligands were purchased from Sigma-Aldrich Inc. (St. Louis, Mo.). Pure dimethyl sulfoxide and triethylamine were purchased from Acros Organics (Pittsburgh, Pa.). 1,4-Cyclohexanediol diglycidyl ether as the cross-linker in the generation of Amikabeads-drug complex and ammonia sulfate as the solvent of pDNA binding were both purchased from Sigma-Aldrich Inc. (St. Louis, Mo.). EB buffer (10 mM Tris-Cl) was purchased from Acros Organics (Pittsburgh, Pa.).

Preparation of Unmethylated Plasmid

*E. coli* K12 ER2925 and GM272 were used to generate the unmethylated pGL4.5 plasmid; GM272 bacterial strain was generously provided by Prof. David Nielsen (Arizona State University, Tempe, Ariz.). The *E. coli* ER 2925 and GM272 strains lack the DNA adenine methyltransferase (Dam) and DNA cytosine methyltransferase (Dcm), [17-19] which methylate the adenine or internal cytosine in GATC or CCNGG (N is A or T), respectively, in *E. coli*. Competent ER2925 and GM272 *E. coli* strains were prepared using the Mix & Go *E. coli* Transformation Kit & Buffer Set; these cells were then used for transformation of the pGL4.5 plasmid via the heat shock method. Briefly, 1-2 µL of plasmid DNA (150 ng/µL) were gently mixed with 10-20 µL of competent cells in a 1.5 mL micro-centrifuge tube and the mixture was incubated for 20 minutes on ice. The plasmid-*E. coli* mixture was then heat shocked at 42° C. for 45 s, following which the tubes were placed on ice for 3 minutes. LB media (800 µL) was then added to each tube and the tubes were rotated on a shaker at 37° C. and 200 rpm for 3 hours. The cells were then centrifuged at 10,000 rcf for 1 minute at room temperature (~25° C.) following which, most of the supernatant discarded and the remainder of the supernatant and cells were plated on LB+Ampicillin (100 mg/L) agar plates overnight. Individual colonies were selected the following day and grown in liquid media (LB+Ampicillin) for 16 h at 37° C. and 200 rpm following which, the unmethylated plasmid was extracted using the Qiagen Plasmid Giga Kit.

Preparation of Unmodified Amikagel Microbeads (Amikabeads)

Amikagel microbeads (Amikabeads) were prepared through an emulsion polymerization technique. In specific terms, Amikacin hydrate and poly ethylene glycol diglycidyl ether (PEGDE) were mixed in a mole ratio of 1:2 in nanopure water to generate pre-gel solution; polymerization of the pre-gel solution was achieved through introducing a certain amount of heat to the solution; a stable microemulsion system was reached by decently syringing the polymerized solution in the mineral oil-span 80 system. Oil was washed off from the surface of beads by adding ~1% (v/v) Tween-20 to solution and followed by centrifugal process for 10 minutes at 5000 g. Unmodified Amikabeads were obtained from further multiple washes with nanopure water. While the protocol of generating and modifying Amikagel Microbeads (Amikabeads) has been described in the previous research, the type of Amikabeads used in this research were Amikabeads-P (P: Parental) which indicated the microbeads are directly utilized without modification. The size of Amikabeads was averaged by randomly choosing 50 beads from each batch.

Generation of Drug-Conjugated Amikabeads

Berenil (100 mg, 516 g/mol) and doxorubicin (100 mg, 543 g/mol) were separately dissolved in 10 mL of pure dimethyl sulfoxide (DMSO) followed by an addition of 50 µL triethylamine (TEA) at the same mole ratio. Both stock mixtures containing the ligands (doxorubicin or berenil), DMSO and TEA at a concentration of 10 mg/mL were stored in 20 mL glass vials at 4° C. and covered by aluminum foil in order to protect the contents from light.

The generation of drug-conjugated Amikabeads was carried out in two steps. In the first step, 10 mg of DNA-binding ligands (doxorubicin or berenil) were collected from the stock solution, followed by an addition of 1,4-cyclohexanediol diglycidylether (1,4-CHDDE) and trimethylamine (TEA) at a mole ratio of 1:3:5. DMSO was added to the mixture in order to obtain a final volume of 2 mL. In light of the chemical inactivity between Amikabeads and DNA-binding ligands, a cross-linker was employed to connect both compounds for completing the conjugation process. In some embodiment, 1,4-CHDDE was used as the linker. After the mixing, the ligand-linker solution was stirred away from light at 320 rpm for 8 hours. The conjugation process was completed by transferring unmodified Amikabeads (1 mg) to the prepared ligand-linker solution and placing the mixture away from light for 24 hours at 320 rpm and 65° C., leading to the formation of drug-conjugated Amikabeads. Drug-conjugated Amikabeads were washed three times with dimethyl sulfoxide (DMSO) before further use. Both differential interference contrast and phase-contrast microscopy images of drug-conjugated Amikabeads were obtained, and their diameters were determined and averaged using statistical techniques. Doxorubicin- and berenil-conjugated Amikabeads are henceforth termed doxo-beads and berenil-beads, respectively. In addition, the logarithmic form of octanol-water partition coefficient (log P value), used as an indicator of lipophilicity/hydrophobicity, was measured for both doxorubicin and berenil using Molinspiration Chemoinformaics online database.

Determination of Amine Content and Ligand Density for Drug-Conjugated Amikabeads The content of reactive amines in ligand-conjugated Amikabeads was used as an indicator of reactive groups left over after conjugation, and was determined using the ninhydrin assay. Drug-conjugated Amikabeads were collected and washed three times with DMSO in order to remove any unreacted ligands. After drying the complex, 1 mL of nanopure water was added to the both containers, which was followed by the addition of ninhydrin assay reagent (100 µL) to 1 mg/mL of sample dispersion. The mixture was boiled at 100° C. for 5 minutes following which, the absorbance at 570 nm was determined using a BioTek Synergy 2 instrument. The content of reactive amines present in drug-conjugated Amikabeads was determined by comparing the absorbance value for the ligand-conjugated Amikabeads with respect to a calibration curve generated using glycine standards.

Presence of reactive amines on Amikabeads enables the subsequent conjugation of DNA-binding ligands, and the amount of ligand bound on the Amikabeads (ligand density) was eventually employed to determine DNA binding. In this study, 10 mg of DNA-binding ligands (doxorubicin and berenil) were conjugated with 1 mg of unmodified Amikabeads using the approach specified in the previous section. Following the conjugation, the mixture was centrifuged to separate the conjugated Amikabeads and unreacted ligands. The supernatant was collected and diluted to 100-fold in order to match the standard calibration range. The diluted supernatant was measured by BioTek Synergy 2 Luminometer at 500 nm wavelength for doxorubicin and at 375 nm wavelength for berenil. The value was fitted into a standard calibration curve prepared based on each DNA-binding ligand in order to obtain the amount of unreacted ligand left on the supernatant. The amount of bound ligand was determined using mass balance and the value was converted to the ligand density of each DNA-binding ligand based on 1 mg of conjugated Amikabeads.

Plasmid DNA Binding to Drug-Conjugated Amikabeads.

Drug-conjugated Amikabeads (0.1 mg) were incubated with 10,000 ng-250,000 ng of pGL4.5 (DH5-α) plasmid DNA in 1 mL of buffer I solution (1.3 M $(NH_4)_2SO_4$ in 10 mM Tris-Cl, pH 8.5) at room temperature (~25° C.) for 24 hours. The same procedure was also carried out for two unmethylated plasmids obtained from GM 272 and ER 2925 strains. The binding of pDNA to ligand-conjugated Amikabeads was facilitated by the high salt concentration (1.3 M), which was similar to the operation in hydrophobic interaction chromatography (HIC). A NanoDrop spectrophotometer was employed to determine the concentration of free pDNA in the supernatant. Binding of the methylated pGL4.5 plasmid, obtained from the DH5-α *E. coli* strain, on unmodified (parental) Amikabeads was investigated as a control.

The amount of pDNA adsorbed on the drug-conjugated Amikabeads (or unmodified Amikabeads) was determined using mass balance. An adsorption isotherm was developed by plotting the amount of absorbed pDNA against the corresponding concentration of free pDNA in the supernatant at equilibrium. The adsorption isotherm was fitted to the Langmuir isotherm model using the expression shown below:

$$Q_e = \frac{K_c C_e}{1 + K_c C_e} * Q_{max}$$

In the above equation, $Q_e$=amount of pDNA bound to the conjugated doxo-beads at equilibrium (µg/mg), $C_e$=concentration of pDNA in the solution at equilibrium (mg/L), $K_L$=Langmuir adsorption constant (L/mg). The Langmuir constant was an indicator of characterizing the affinity of binding sites to the given solute from the mixture at equilibrium. $Q_{max}$=maximum amount of pDNA adsorbed onto the ligand-functionalized Amikabeads (µg/mg). The linearized form of Langmuir model, in which $1/Q_e$ was plotted as a function of $1/C_e$ as shown below, was employed to determine the isotherm parameters:

$$\frac{1}{Q_e} = \frac{1}{Q_{max} * K_c} \frac{1}{C_e} + \frac{1}{Q_{max}}$$

In this approach, the slope of the linear plot represents the reciprocal of the product of the maximum binding capacity and Langmuir constant, whereas the value of maximum binding capacity can be determined from the intercept. The coefficient of determination (R-square value) was obtained in each case of binding to investigate the fitting of experimental data to the Langmuir isotherm model. The R-square value represents the percent of data that is the best fit to the model.

Desorption of Bound pDNA from Drug-Conjugated Amikabeads

Ligand-conjugated Amikabeads (~0.1 mg) were loaded with 250,000 ng plasmid DNA in order to ensure that the adsorption was in the non-linear portion of the isotherm for both methylated and unmethylated investigations. Plasmid DNA-bound Amikabeads were first washed with buffer I in order to remove excess free pDNA content from supernatant. 10 mM Tris-Cl at pH 8.5 was employed as the 0 M of buffer I in the eluent buffer. In addition to modulating the salt concentration, various organic modifiers were added to the eluent for potentially enhancing the desorption of pDNA. Organic modifiers including methanol, ethanol, isopropyl alcohol, butanol and acetonitrile were used as a 15% (v/v) mixture with 10 mM Tris-Cl at pH 8.5. All desorption steps were carried out for 24 hours at room temperature (~25° C.), following which, the mixture was gently centrifuged and the pDNA content in the supernatant was determined using a NanoDrop spectrophotometer. The amount of pDNA desorbed from ligand-conjugated Amikabeads was determined using mass balance.

The aminoglycoside antibiotics including amikacin, streptomycin, neomycin, kanamycin, tobramycin and gentamicin are used to treat the bacterial infection caused by gram-negative organisms. The antibiotics stops the bacterial activities by binding and stabilizing the 16s RNA and reacting with 30s subunit of bacterial ribosome, which results in an inhibition of protein synthesis. The natural affinity towards the nucleic acid provides the compound a great potential in generating various products in nucleic acid biotechnology. In our previous work, we developed aminoglycoside microbeads for plasmid DNA binding and recovery. Here, we report the generation of anti-neoplastic chemotherapeutic drug-conjugated Amikabeads as potential hydrophobic interaction chromatography resins for DNA binding and recovery. These modified beads hold great potential in selectively recovering hypermethylated genomic DNA from cell lysates towards their application in next-gen cancer diagnostics. As a proof of concept, we show the binding and recovery of plasmid DNA (pGL4.5) to the doxorubicin and berenil conjugated Amikabeads.

Figure 1B:
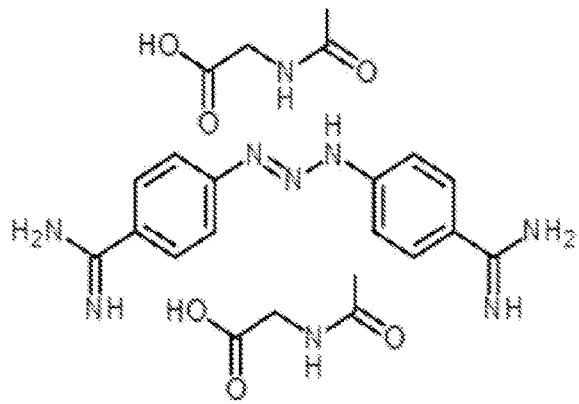
Figure 2:
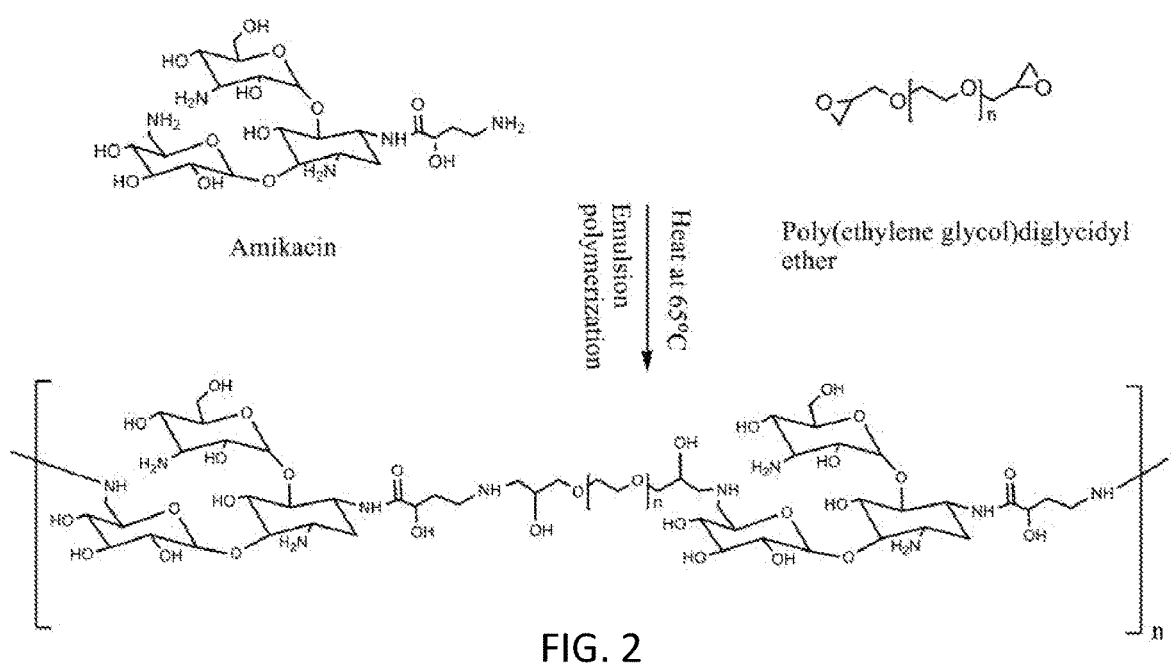
FIG. 2: Schematic of generation of Amikabeads through emulsion polymerization of amikacin hydrate and poly (ethylene glycol) diglycidyl ether (PEGDE).

As mentioned before, DNA specific ligands doxorubicin and berenil have been conjugated to Amikabeads to develop novel DNA binding resins for multiple applications in nucleic acid biotechnology and cancer diagnostics (FIGS. 1A-B). These DNA-ligands are highly specific towards the nucleic acids and bind to the DNA via intercalation. As shown in FIG. 2, unmodified Amikabeads were generated through the emulsion polymerization reaction between amine contained amikacin hydrate and PEGDE. Although the abundant presence of primary amine groups on the Amikabeads surface renders the compound easier to react, a direct reaction between doxorubicin or berenil and Amikabeads cannot occur. Spacer molecules such as 1,4-Cyclohexanediol diglycidyl ether (CHDDE) were used to connect doxorubicin, berenil and the Amikabeads.

In certain embodiments, other examples of crosslinkers that can be used as spacer moieties include but are not limited to -(1,4-cyclohexane dimethanol diglycidyl ether, Neopentylglycol diglycidyl ether, 1,4-butanediol diglycidyl ether, ethylene glycol diglycidyl ether, polypropylene glycol diglycidyl ether, resorcinol diglycidyl ether, glycerol diglycidyl ether, polyethylene glycol diglycidyl ether), polymethyl methacrylate, polyethylene glycol methyl ether, polyethylene glycol diacrylate, polyethylene glycol diamine, Poly(2-hydroxyethyl methacrylate), Poly(D,L-lactide-co-glycolide), poly-lactic acid, poly-glycolic acid, Poly[(R)-3-hydroxybutyric acid], Poly(dimethylsiloxane), vinyl terminated, Poly(dimethylsiloxane), and diglycidyl ether terminated.

The initial trials of the generating of doxo-beads by reacting unmodified Amikabeads with cross-linker before addition of doxorubicin/berenil resulted in an aggregation of microbeads. This was likely caused by the epoxide containing crosslinker connecting and crosslinking the amines in adjacent Amikabeads. In order to avoid the crosslinking, we derivatized doxorubicin and berenil with diglycidyl ether, which resulted in mono and bi-functionalized doxorubicin-DE conjugates. Mono and bi-functionalized doxorubicin-DE conjugates were then added to unmodified Amikabeads, resulting in minimal aggregation and generation of doxorubicin/berenil conjugated Amikabeads. The non-aggregated doxo-beads complex (FIGS. 3A-C) was generated after adding the prewashed unmodified Amikabeads to the doxo-linker solution for 24 hours at 65° C. The doxo-linker solution was prepared by conjugating cross-linker, 1,4-cyclohexanediol diglycidyl (1,4-CHDDE) with doxorubicin and triethylamine as the catalyst in a mole ratio of (1:3:5) for 8 hours at room temperature. The mole ratios of the constituents modified to minimize aggregation.

In certain embodiments, other CG region binding drugs that could be conjugated to Amikabeads include but are not limited to Table 1, which shows the list of small molecules and anticancer drugs that can be attached to Amikabeads and Amikagel monolithic columns for novel mixed-mode pDNA chromatographic resins.

TABLE 1

| ID | Small molecules |
|---|---|
| 1 | Doxorubicin |
| 2 | Mitoxantrone |
| 3 | Daunomycin |
| 4 | Amonafide |
| 5 | Etoposide |
| 6 | Adenine |
| 7 | Guanine |
| 8 | Cyclosporamide |
| 9 | Vincristine |
| 10 | Netropsin |
| 11 | Furamidines |
| 12 | Ethidium bromide |
| 13 | Proflavine |
| 14 | Epirubicin |
| 15 | 8-Aminoacridine |
| 16 | Mitomycin |
| 17 | Distamycin |

TABLE 1-continued

| ID | Small molecules |
|---|---|
| 18 | Idarubicin |
| 19 | Valrubicin |
| 20 | Pixantrone |
| 21 | Bleomycin |
| 22 | Methotrexate |

In certain embodiments, the hypermethylated DNA could be isolated by modifying the hydrophobicity of the resins bound to the Amikabeads. These resins already target the CG rich regions of the genomic DNA and modifying their hydrophobicities allows for the targeting and selective binding of hypermethylated CpG islands versus non-hypermethylated CG islands. Drugs bound to the resins could be easily modified to increase their hydrophobicities via addition of the following moieties through solid phase chemistries. Hydroxyls on the drug molecules can be reacted with different alkyl chlorides to rapidly generate a library of derivatized ligands capable of binding hypermethylated DNA. These acid chlorides can be reacted with the drug conjugated-Amikabead resins at room temperature, in DMSO and in presence of TEA.

Possible modifiers that can be used to tune the hydrophobicity of the resins include but are not limited to Long chain and short chain alkyl, aryl, piperazinyl, piperidyl, pyrrolidyl groups.

Figure 3A:
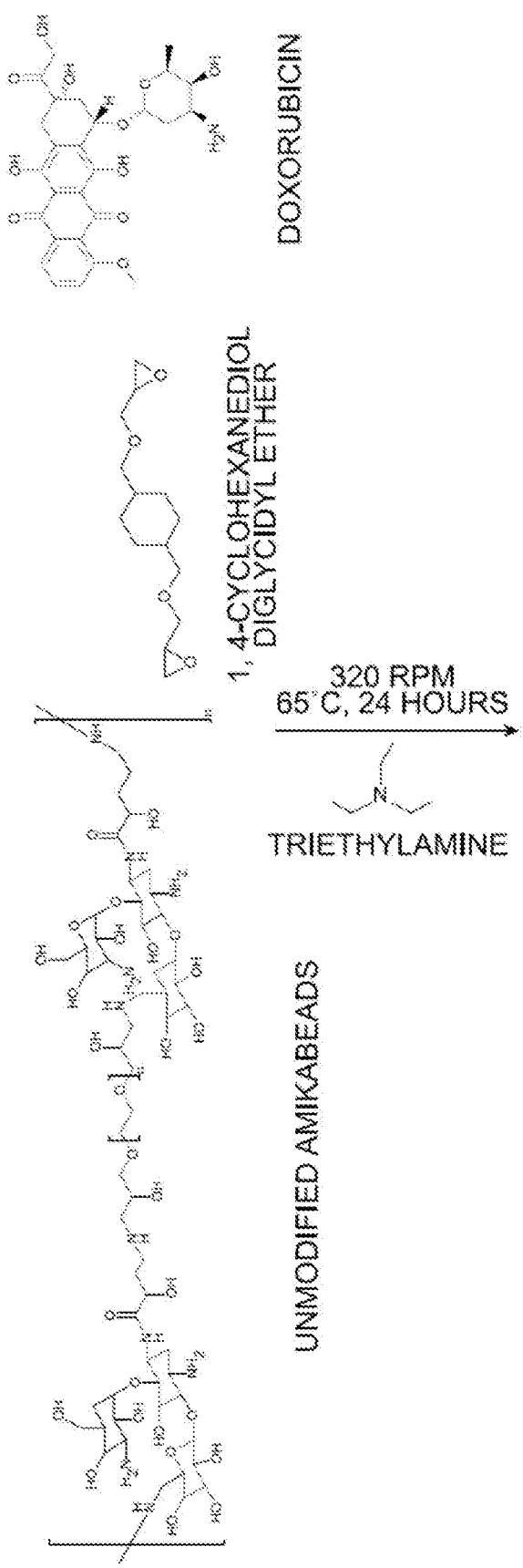
FIGS. 3A-C: Schematics of the generation of doxo-beads obtained by conjugating (A) doxorubicin and (B) Berenil to Amikabeads using 1,4-cyclohexanedio diglycidylether as a cross-linker. Structures were referenced from Sigma-Aldrich online database and redrawn using ChemDraw. (C) Conjugation of monofunctionalized DNA binding ligands to Amikabeads or macroporous Amikagels. Solid-phase combinatorial synthesis methods will be employed to rapidly generate and screen a library of derivatized ligands (selected R-groups are shown) that can demonstrate higher selectivity to hypermethylated DNA compared to unmethylated DNA.
Figure 3A:
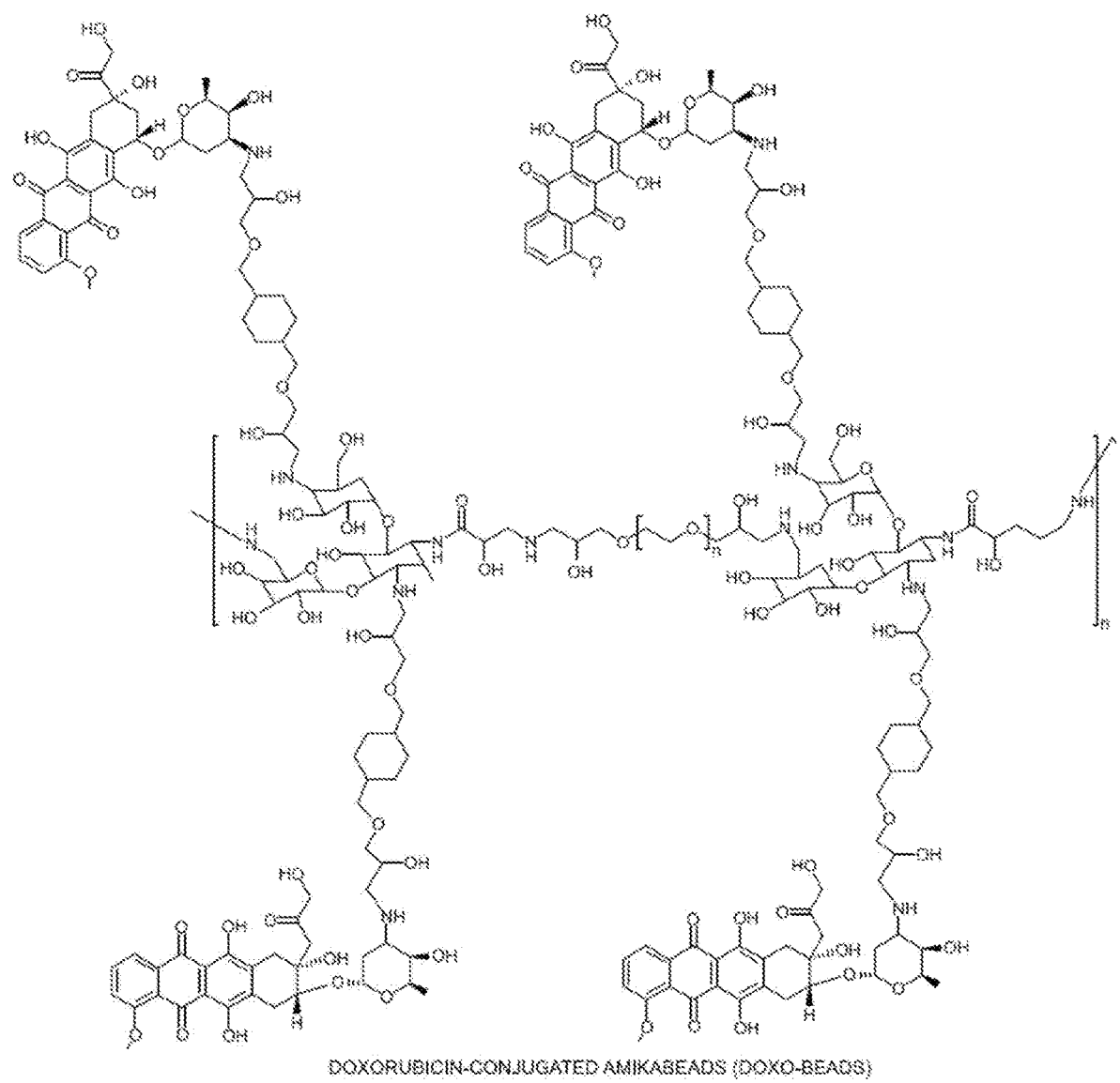
Figure 3B:
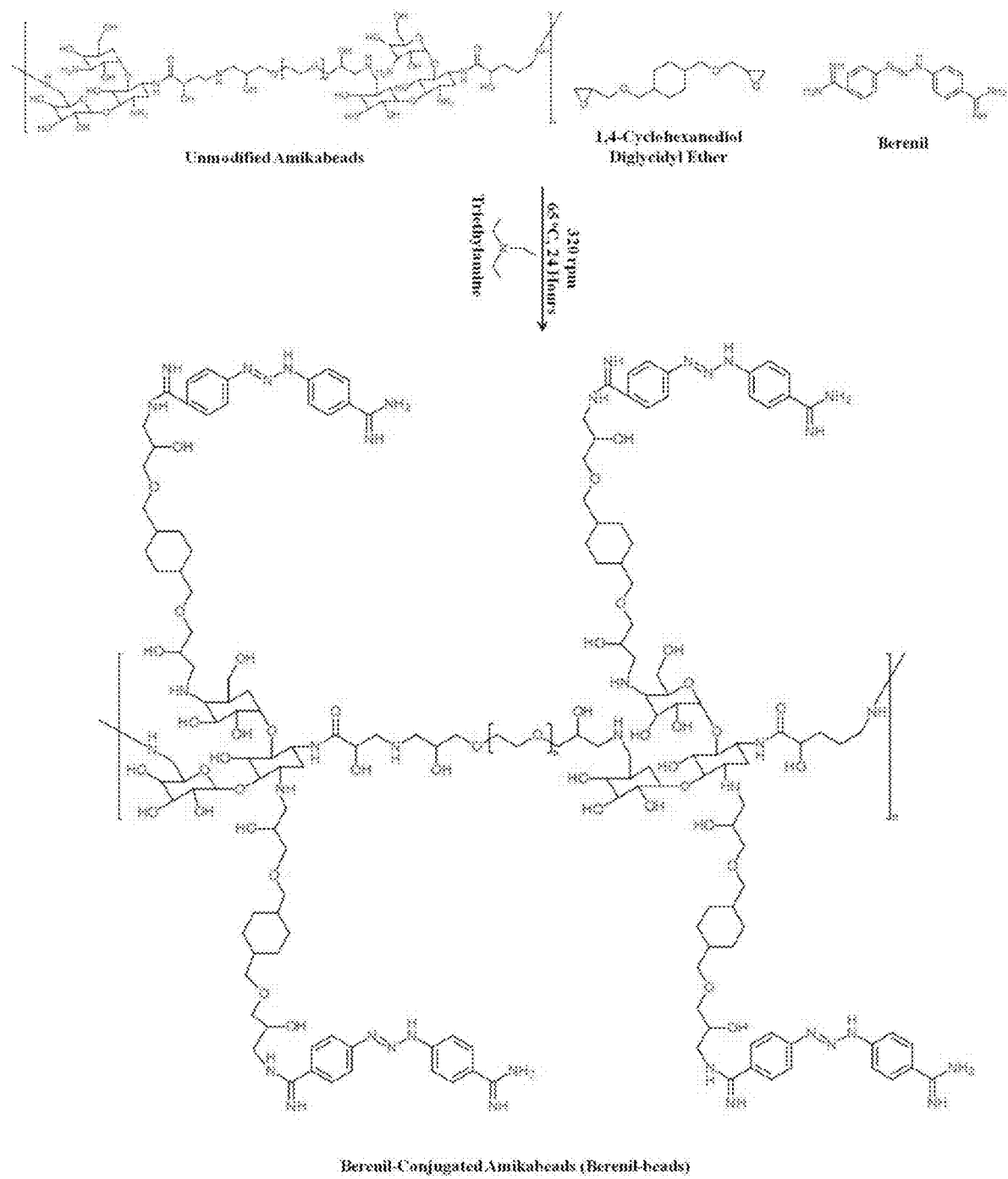
Figure 3C:
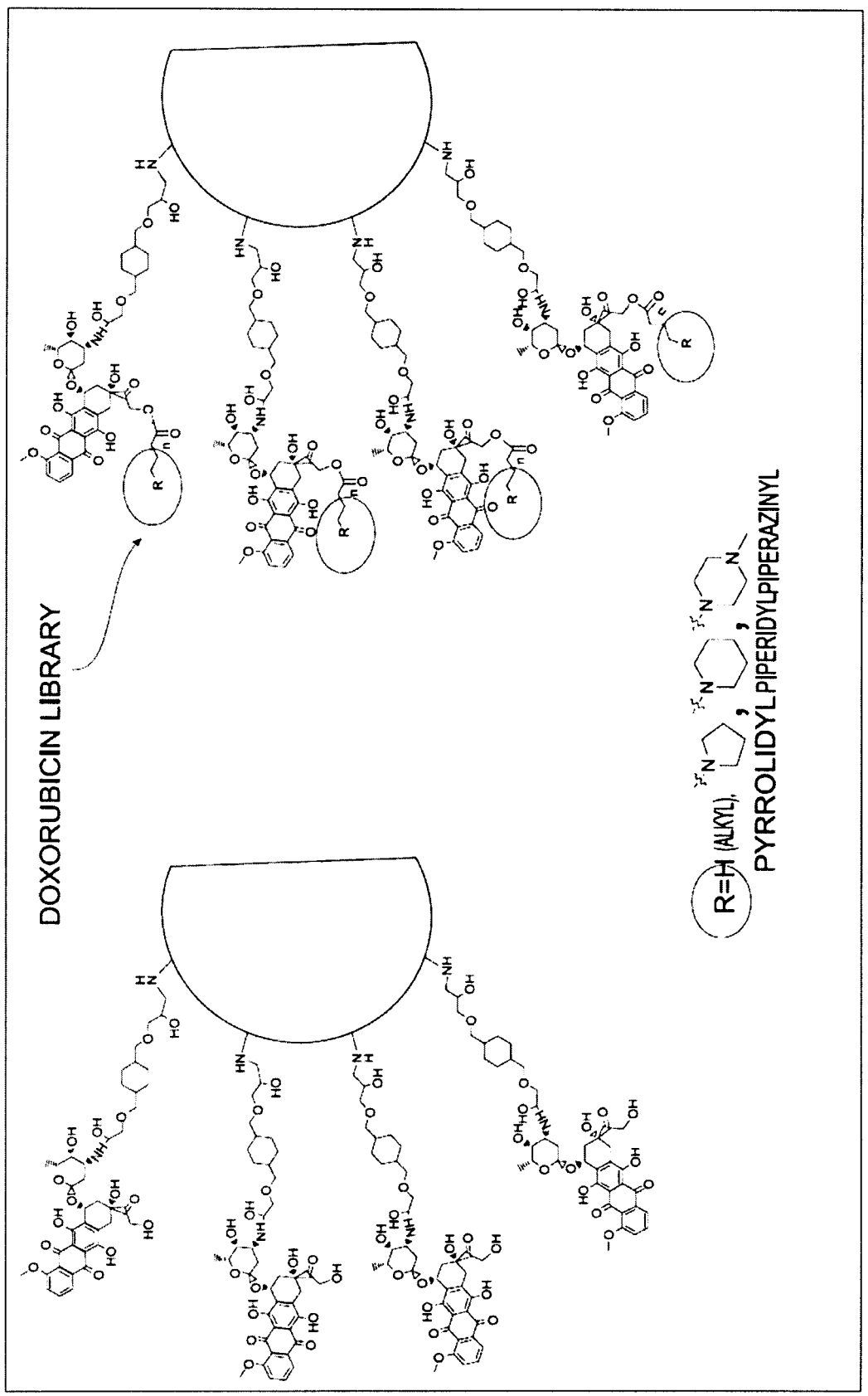

FIG. 3C shows the schematic for conjugating the hydrophobic modifiers to small molecule drug conjugated Amikabead resins.

Generation and Characterization of Drug-Conjugated Amikabeads

Parental (unmodified) Amikabeads were generated via an emulsion polymerization reaction between amikacin hydrate and PEGDE (FIG. 2). Doxorubicin and berenil, used as DNA-binding ligands in this study, were conjugated to parental Amikabeads using 1,4-cyclohexanediol diglycidylether as a linker. The conjugation reaction involved the opening of epoxide groups in the cross-linker by primary amine groups on the surface of unmodified Amikabeads and DNA-ligands molecules (FIGS. 3A and 3B).

The shape and appearance of drug-conjugated Amikabeads/Amikaliths were compared to the shape and appearance of unmodified Amikabeads/Amikaliths as shown in FIG. 4A. FIG. 4A, shows the clean, non-aggregated unmodified Amikabeads generated as the desired candidate for pDNA purification. Minimal aggregation among beads will likely prevent reduction in surface area for pDNA binding. Previous research has shown that the pDNA binding can be significantly affected by employing the aggregated Amikabeads due to the decrease of surface area to volume ratio. Fluorescence of doxorubicin-conjugated Amikabeads was monitored to understand the distribution of the ligand across the Amikabead. As shown in FIG. 4b, doxorubicin-ligand was uniformly distributed across the Amikabead. The color of doxo-beads and berenil-beads dissolved in DMSO solvent was observed like red and yellow, respectively (FIG. 6A), meanwhile, the dark red and yellow pellets left in the tube (FIG. 6B) from high-speed centrifugal process verified the hypothesis and indicated the drug-conjugated Amikabeads were successfully generated.

Figure 5A:
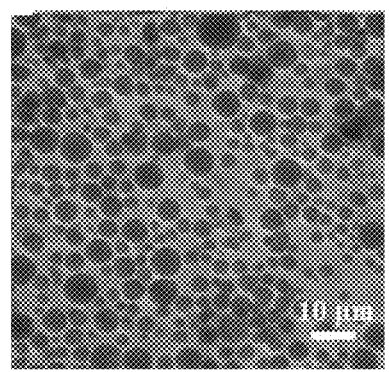
FIGS. 5A-B: Microscopic view of berenil-beads (A) and doxo-beads (B) after conjugating the cross-linker with antineoplastic drug (dark spots on both images) followed by adding the unmodified Amikabeads. Both microbeads presented a clean appearance and minimum aggregation.

Amine content of Amikabeads was monitored before and after ligand modifications. We hypothesize that the conjugation reaction between anti-neoplastic drugs and Amikabeads was through the epoxy and reactive primary amines on Amikabeads, and the generated doxorubicin-beads should contain lesser free primary amine groups on the surface after the conjugation process was completed. In order to determine the amine content on the drug-conjugated Amikabeads, ninhydrin assay was performed to examine the presence of primary amine on the microbeads surface. The reaction of 1 mg drug-conjugated Amikabeads model with 100 ul of ninhydrin assay reagent resulted in the light yellow color throughout the microbeads compared to the result of bluish-purple color represented in the unmodified Amikabeads via the same ninhydrin reaction (FIG. 6C). The light yellow color in the drug-conjugated Amikabeads batch indicated the absence of a primary amine group after ligand conjugation whereas the bluish-purple color in the unmodified Amikabeads batch represented the presence of a primary amine group. Drug-conjugated Amikabeads were further visualized using differential interference contrast (DIC) microscopy (FIG. 5). As seen in the figure, doxo-beads and berenil-beads were similar in diameter to parental Amikabeads (Table 2), and negligible aggregation of the beads was seen following conjugation of the DNA-binding drugs. The density of the drug conjugated on Amikabeads (ligand density), was determined using spectrophotometer and mass balance, and as is shown in Table 2.

TABLE 1

Langmuir adsorption isotherm parameters for pGL 4.5 plasmid DNA (methylated plasmid obtained from the DH5-α E. coli strain) binding onto drug-conjugated Amikabeads and parental (unmodified) Amikabeads at 25° C.

| Type of Amika-beads | Average Beads Size (μm)$^a$ | $Q_{max}$ (μg/mg) | $K_L$ (L/mg) | $R^{2(*)}$ | Ligand Density (mmol/mg of Amikabeads) |
|---|---|---|---|---|---|
| Doxo-beads | 8.05 ± 1.08 | 166 ± 14 | 0.018 ± 0.01 | 0.96 | 12.1 ± 0.27 |
| Berenil-Beads | 7.25 ± 2.56 | 121 ± 21 | 0.016 ± 0.01 | 0.94 | 13.3 ± 0.45 |
| Parental-Beads | 9.5 ± 2.12 | 42.9 ± 10 | 0.230 ± 0.18 | 0.93 | N/A |

$^{(*)}R^2$ represents the coefficient of determination for the linear relationship on fitting experimental data shown in FIGS. 4A-C to the Langmuir isotherm model.
$^a$Average beads size was determined by calculating the average diameter of >50 microbeads in one microscopic screenshot image.

pDNA on Drug-Conjugated and Parental Amikabeads: Binding and Elution

Binding of pDNA onto drug-conjugated Amikabeads was investigated using a batch adsorption assay. The pGL4.5 plasmid, which express the luciferase protein under the control of SV40 promoter, was processed through DH5-E. coli, which contains enzymes such as Hsd, Dam and Dcm methylases that methylate the plasmid. Our initial investigation on the adsorption of this methylated plasmid on drug-conjugated Amikabeads demonstrated a minimal binding effect under low salt conditions, similar to those used in ion-exchange chromatography (not shown). We therefore investigated the hydrophobic interaction chromatography (HIC) mode as a potential approach in which a high concentration of salt was employed to drive pDNA adsorption onto drug-modified Amikabeads. We hypothesize that the adsorption process is facilitated by the hydrophobic interaction between drug-conjugated microbeads and hydrophobic regions of pDNA grooves.

Figure 7:
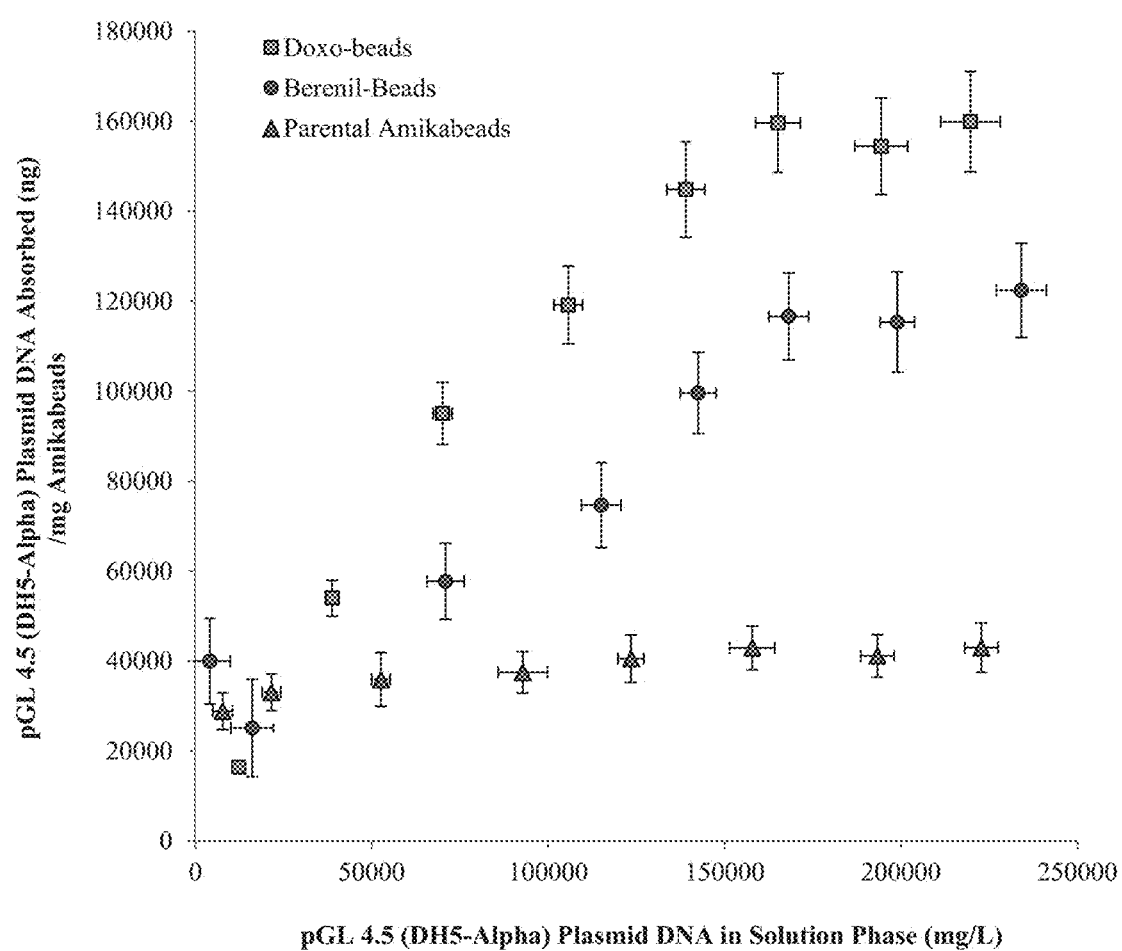
FIG. 7: Adsorption Isotherm of pGL 4.5 plasmid DNA processed using the DH5-α $E.$ $coli$ strain onto drug-conjugated Amikabeads in the presence of 1.3 M $(NH_2)SO_4$ in 10 mM Tris-Cl, pH 8.5 at room temperature (~25° C.) for 24 hours. These data were fit to a Langmuir isothermal model and the isotherm parameters are shown in Table 2. The data represent a mean of n=4 experiments and error bars indicate one standard deviation around the mean.

The binding of pDNA on drug-conjugated Amikabeads was visualized using florescence microscopy (FIGS. 10A-D). Quantitative data on pDNA binding were obtained using batch adsorption assay in which, the amount of pDNA bound to the drug-conjugated Amikabeads at equilibrium was plotted against the concentration of unbound pDNA in the supernatant (FIG. 7). The data were fit to a Langmuir adsorption isotherm model in order to obtain adsorption parameters including the maximum binding capacity ($Q_{max}$), and Langmuir constant, $K_L$. The $Q_{max}$ and $K_L$ values for pDNA adsorption on doxo-beads were 166 µg pDNA/mg of doxo-beads and 0.018 L/mg, respectively, whereas The $Q_{max}$ and $K_L$ values for pDNA adsorption on berenil-beads were 121 µg pDNA/mg of berenil-beads and 0.016 L/mg, respectively (Table 2). A comparison of $Q_{max}$ values indicated higher binding capacity of doxo-beads to berenil-beads, which is likely due to the higher binding affinity/greater selectivity of the anticancer drug to the pDNA compared to that demonstrated by berenil. The amine in the aminosugar moiety of free doxorubicin has been shown to interact with the AT-rich groove while the rest of the molecule intercalates within the GC region of the DNA. However, the amine in the doxorubicin is conjugated to Amikabeads, which makes it unlikely for the aminosugar moiety to be available for interacting with DNA. The interaction of doxo-beads with DNA is hence largely based on hydrophobic and hydrogen bonding interactions, which essentially govern the binding under these conditions due to the unavailability of the amine moiety for ionic interaction. Use of a lower salt concentration, i.e. 10 mM Tris-Cl (pH 8.5), resulted in minimal binding of pDNA to doxo-beads (not shown), which further indicated minimal contribution of Coulombic interactions to the bindings. On the other hand, berenil interacts with DNA using a combination of Coulombic, hydrogen bonding, and hydrophobic interactions. At high concentrations of ammonium sulfate, Coulombic interactions are largely shielded and the hydrophobic interactions may not be as strong as those with doxorubicin.

Some indication of the role of hydrophobicity can be further obtained from the log P value for both ligands. The log P value of a drug is defined as the ratio of the concentration of a compound in an organic phase (octanol) to aqueous phase (water) at equilibrium and is used as an indicator of lipophilicity/hydrophobicity of the compound. The higher log P value of doxorubicin (0.57) compared to that of berenil (0.39) indicates a higher lipophilicity of the former (FIG. 2), and is in part responsible for higher pDNA binding seen with the anticancer drug.

It is worth noting that although the KL value (0.23 L/mg) of the parental-Amikabeads was higher than that for doxo-beads (0.018 L/mg) and berenil-beads (0.016 L/mg), the maximum binding capacity of parental-Amikabeads (42.9 µg/mg) was distinctly lower than the drug-conjugated derivatives. This is likely because the amine group in parental (unmodified) Amikabeads are hydrophilic and therefore less effective in binding pDNA by means of hydrophobic interactions under the binding condition employed. Desorption of pDNA from Drug-Conjugated Amikabeads.

Desorption of biomolecules in HIC systems is carried out using buffers with low salt concentration, which facilitates unbinding of the biomolecule from the hydrophobic material and resolubilization in the aqueous supernatant. Approximately 36% of the initial loaded methylated plasmid DNA was eluted from doxo-beads when equilibrated with 10 mM Tris-Cl at pH 8.5 (Table 3); the initial pDNA loading was in the non-linear part of the adsorption isotherm (FIG. 7). However, only 28% of pDNA was recovered from berenil-beads under the same conditions (Table 3). It is likely that Coulombic interactions between pDNA and berenil-beads at lower salt concentrations are responsible for the increased retention of pDNA on berenil-beads.

TABLE 3

Comparison of desorption performance from drug-conjugated Amikabeads using various organic modifiers at 25° C. In all cases, the EB buffer (10 mM Tris-Cl, pH 8.5) was used.

| Buffer | Modifier Volume Percentage (%) | Doxo-Beads Desorption Percentage (%) | Berenil-Beads Desorption Percentage (%) |
| --- | --- | --- | --- |
| EB Buffer | 0 | 36 ± 3 | 28 ± 5 |
| 1-Butanol | 15 | Bi-Layer | Bi-Layer |
| Isopropyl Alcohol | 15 | 41 ± 6 | 59 ± 6 |
| Ethanol | 15 | 48 ± 10 | 42 ± 2 |
| Methanol | 15 | 55 ± 5 | 40 ± 9 |
| Acetonitrile | 15 | 78 ± 6 | 48 ± 5 |

The hydrophobic aggregation is occurred as the hydrophobic solutes orient away from the surrounded polar molecule (water) in order to maximize the system entropy. Therefore, entropic driving force can be weakened by removing water molecules in the eluent system. We hypothesized that further enhancement of pDNA desorption from drug-conjugated Amikabeads could be facilitated by using organic modifiers in the eluent buffer. Five different organic modifiers including methanol, ethanol, isopropyl alcohol, 1-butanol and acetonitrile were added to 10 mM Tris-Cl at a concentration of 15% (v/v) and their desorption potential was investigated. In the case of doxo-beads, up to 55% of methylated pDNA was eluted using 15% (v/v) methanol as the modifier, whereas nearly 80% of adsorbed pDNA was eluted using acetonitrile (Table 3). This difference can be explained from two aspects of intermolecular interactions. Firstly, methanol is less polar than water, which introduces a disruption to hydrophobic aggregation in the eluent system. However, acetonitrile is significantly less polar than methanol due to the lower electronegativity situated in carbon-nitrogen bond in acetonitrile compared to the carbon-oxygen bond in methanol. Hence, acetonitrile is able to better disrupt the hydrophobic aggregation, thus promoting the desorption when methanol is replaced by acetonitrile in the eluent system. Secondly, besides the hydrophobic interaction, it is likely that pDNA interacts with our resin via hydrogen bonding as well. Hence, better retention of pDNA with the resin could be achieved when more hydrogen bonding is formed in the system. To this extent, retention of DNA could be weakened in the acetonitrile system than methanol system due to less hydrogen bonding comprised in the former. Venables et al. reported that the hydroxyl group in a methanol molecule is capable of accepting two hydroxyl hydrogen atoms while donating one hydroxyl hydrogen atom to the adjacent hydroxyl oxygen atoms. In contrast, acetonitrile molecule is only capable of receiving one hydroxyl hydrogen atoms but is incapable of donating hydroxyl hydrogen atom. The less capability of forming hydrogen bonding in acetonitrile system likely promotes a better elution. These factors likely lead to a better desorption performance using acetonitrile/water system methanol/water system. Further increasing the volume percentage of organic modifier did not result in greater desorption of pDNA, which was consistent with previous observations from the literature; for example, higher pDNA desorption work was reported using 20% (v/v) organic solvent compared to 40% (v/v) from a substrate containing tetraethyl quaternary ammonium groups.

The highest elution of pDNA (59% of initially adsorbed DNA) from berenil-beads was obtained using isopropyl alcohol. The extent of desorption was lower than that observed from doxo-beads using the acetonitrile/water system. This was likely due to the Coulombic interactions that facilitate binding under these conditions. In our previous work, we demonstrated that 15% (v/v) isopropyl alcohol significantly enhanced the amount of pDNA desorbed from Amikabeads that were modified to possess quaternary amines. Tseng et al. also showed that for buffers containing low concentration of alcohol, the overall binding strength between charged molecules diminishes better in the buffer containing longer aliphatic chain due to the domination of increasing hydrophobicity over the alternation of dielectric constant. In addition, the same work also demonstrated the existence of an optimum volume percent for the organic modifier for overcoming hydrophobic interactions of the biomolecule to the solid phase. Effect of the bacterial strain used for pDNA processing.

Figure 8A:
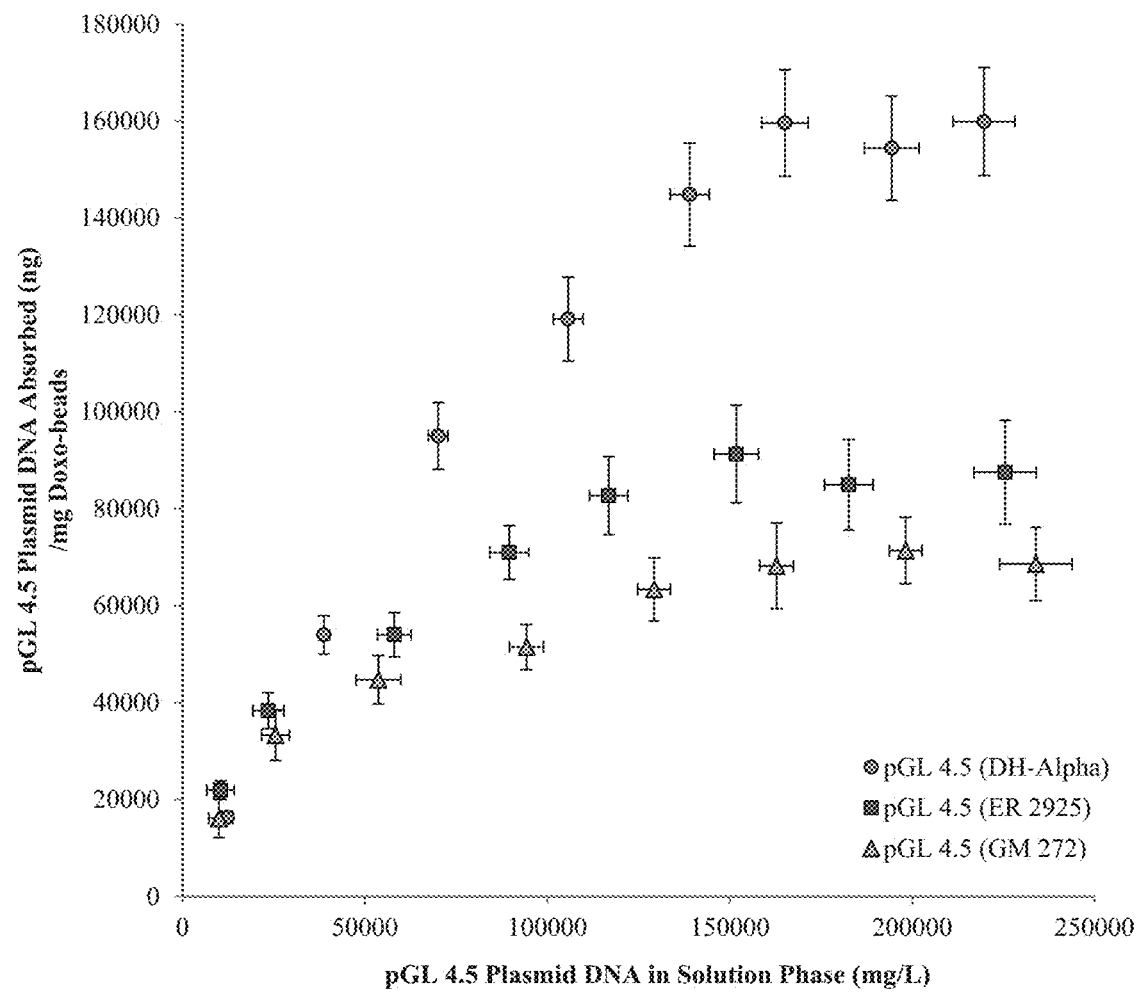
FIGS. 8A & 8B:A) Adsorption Isotherms of different pDNA on doxo-beads at room temperature (~25° C.). Bacterial strains that result in the formation of methylated (e.g. DH5-α $E.$ $coli$) or unmethylated (e.g. $E.$ $coli$ strains GM 272 and ER 2925) were employed. In all cases, adsorption was carried out using 1 mL of buffer I (1.3 M $(NH_2)SO_4$ in 10 mM Tris-Cl, pH 8.5) at room temperature (~25° C.) for 24 hours. The data represent a mean of n=4 experiments and error bars indicate one standard deviation around the mean. B) Desorption (% of initial adsorbed) of pGL 4.5 plasmid DNA, processed in different $E.$ $Coli$ from doxo-beads using methanol or acetonitrile as organic modifiers (15% v/v in 10 mM Tris-Cl buffer).
Figure 8B:
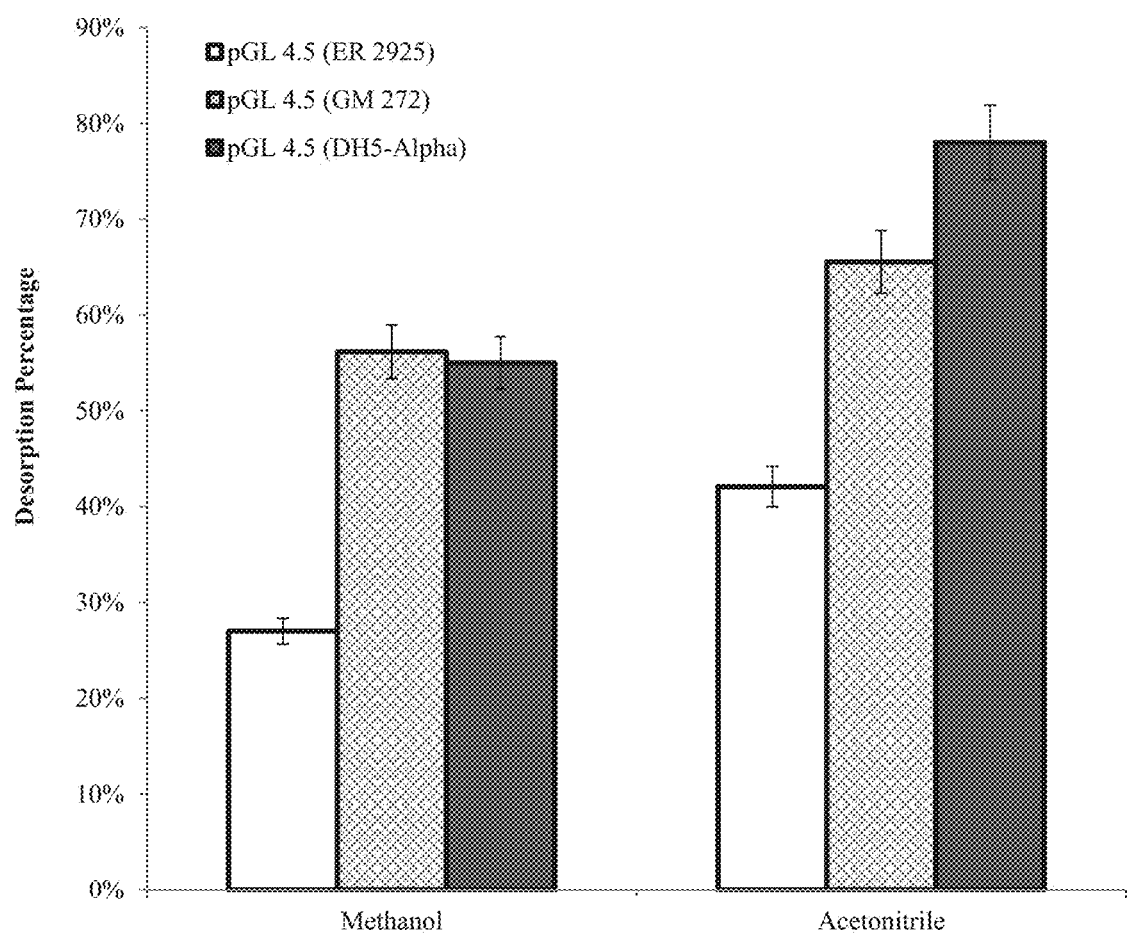
Figure 9:
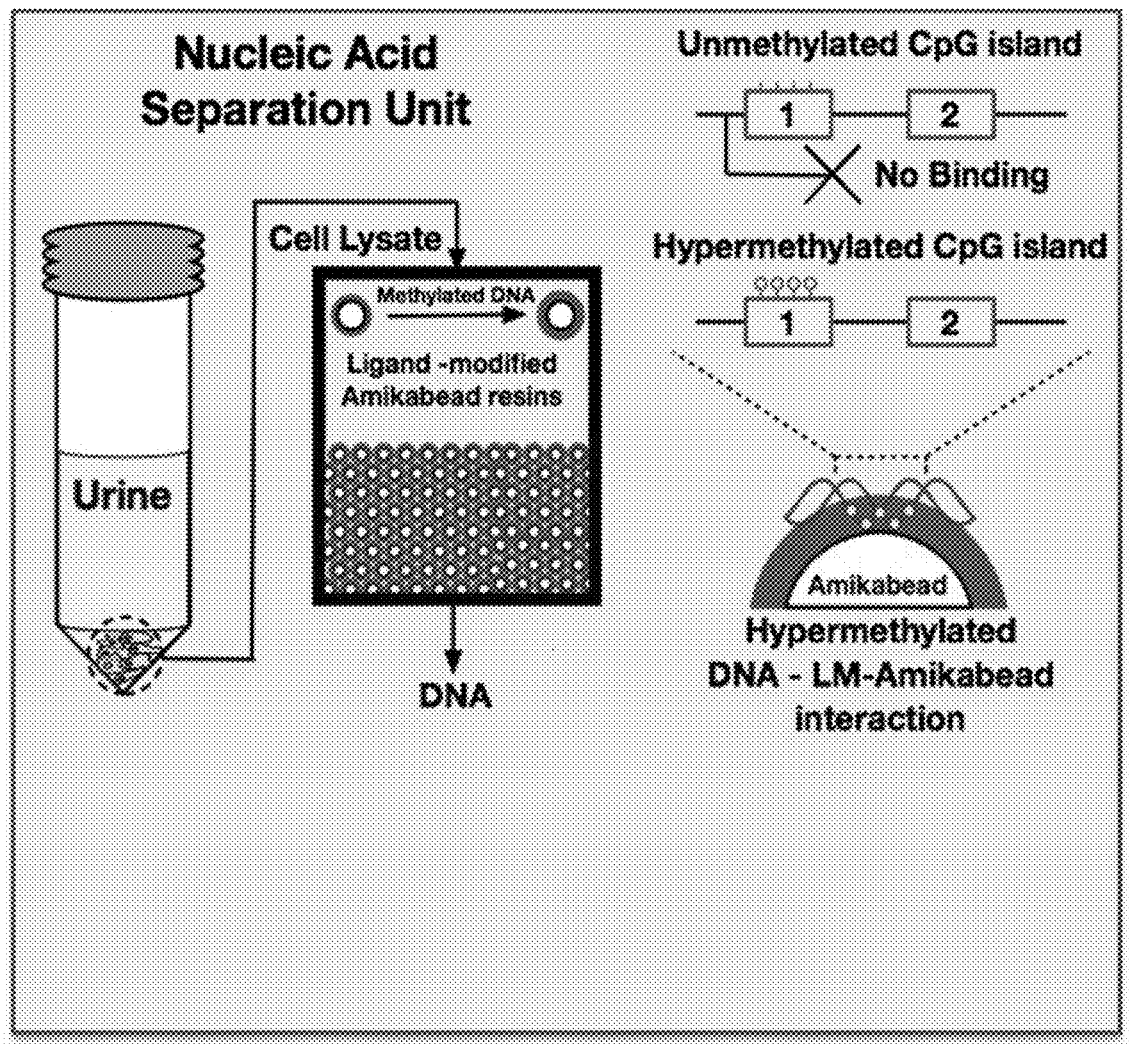
FIG. 9: Molecularly engineered ligands and materials used in a process to selectively enrich hypermethylated DNA from urine.
Figure 10A:
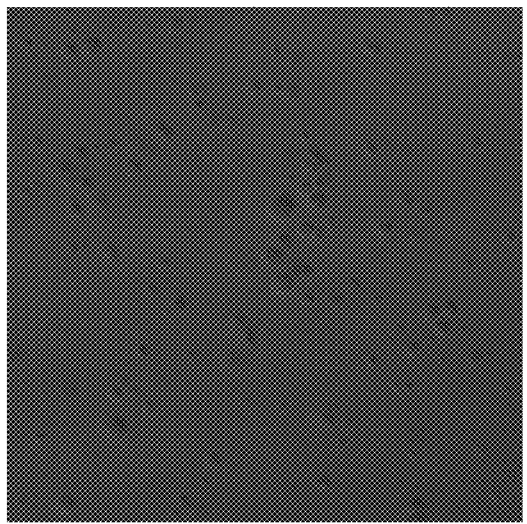
FIGS. 10A-D: (A) and (B): Phase-contrast microscopy of unloaded and pDNA-loaded doxo-beads, respectively. (C) and (D): Fluorescence microscopy of unloaded and pDNA-loaded doxo-beads with pDNA, respectively. The pGL4.5 plasmid, processed using the DH5-α $E.$ $coli$ strain, was used as the pDNA in this experiment. The DNA was stained with DAPI, which results in a pink color following an overlay of the blue-fluorescent DNA and red-fluorescent doxorubicin.
Figure 10B:
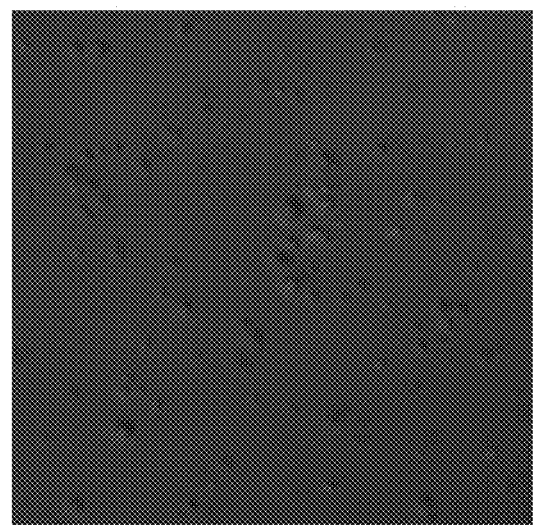
Figure 10C:
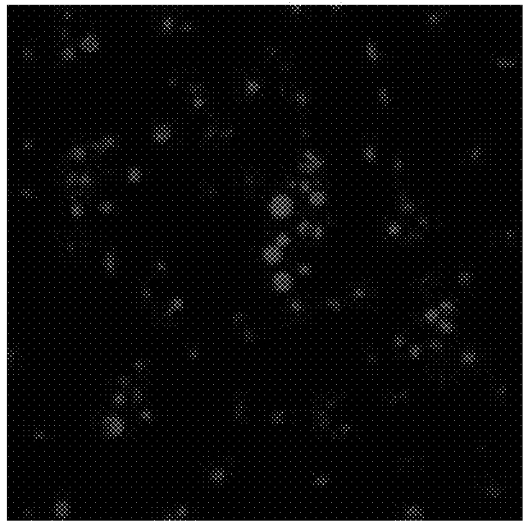
Figure 10D:
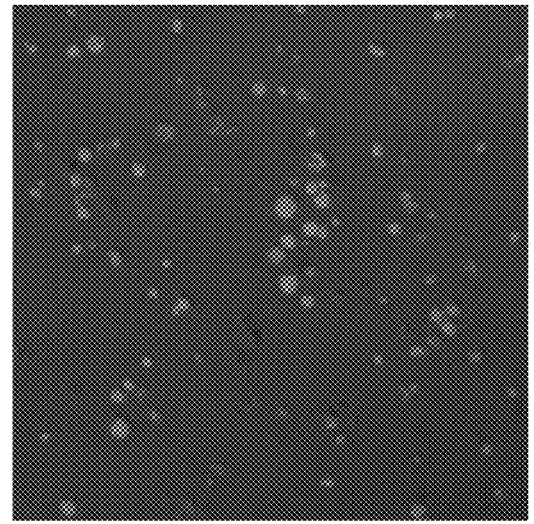

Plasmid DNA processed using routine *E. coli* strains (e.g. DH5-α) is methylated due to the presence of Hsd, Dam and Dcm methylates that methylate the plasmid in the bacteria. We investigated the binding of pDNA processed in GM 272 and ER 2925 strains of *E. coli* that do not possess the enzymes that methylate plasmids, and therefore result in unmethylated plasmids. As shown in FIGS. 8A-B, the maximum binding capacities (Qmax) for pGL4.5 pDNA processed using ER 2925 and GM 272 *E. coli* strains were 88 μg pDNA/mg and 67 μg pDNA/mg, respectively, on doxo-beads. These relatively similar binding capacities, however, are significantly lower than that observed in the case of methylated pDNA generated using DH5-α *E. coli* strain (Qmax=166 μg of pDNA/mg of doxo-beads). The lower binding of unmethylated pDNA can be attributed to the lower hydrophobic interactions of the biomolecule with doxo-beads due to the lack of methyl groups in the unmethylated plasmids. In addition, the absence of the methyl groups can likely result in less efficacious salting out of pDNA in the presence of high salt conditions. Table 3 summarizes the binding effect of drug-conjugated Amikabeads with pGL 4.5 pDNA processed by ER 2925 and GM 272 *E. coli* strains, as a comparison to that from DH5-α *E. coli* strain. In general, DNA methylation is normally occurred in cytosine within CpG islands in gene promoters, which results in silencing gene expresses (e.g. tumor gene expression) as part of epigenetic modification, whereas the CpG islands in gene promoters within normal cells is typically unmethylated. It has been shown that the aberrant DNA methylation relates to an early stage of tumor development and the aberrantly hypermethylated DNA could be detected via whole cell lysates obtained from patient biopsies, urine, blood, sputum and the stool of potential disease patients. In all, the above observed difference in pDNA binding suggests a selectivity of doxo-beads for methylated DNA over unmethylated/hypomethylated DNA, which can have significant implications in technologies, including cancer diagnostics that rely on epigenetic differences.

Figure 5B:
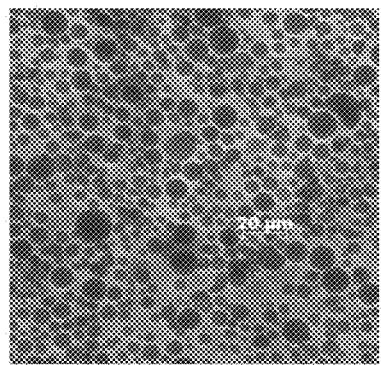

Desorption of pDNA processed from GM 272 ER 2925 *E. coli* was carried out using 10 mM Tris-Cl buffer and methanol or acetonitrile as the organic modifier at a concentration of 15% (v/v), which was similar to methods described previously. Approximately 56% of initially bound GM 272 pGL 4.5 was released using methanol as the modifiers, whereas approximately 66% was eluted with acetonitrile. In the case of ER 2925 *E. coli*, the elution decreased to ~30% in the case of methanol and ~45% in the case of acetonitrile (FIG. 5B). It is likely that the adsorption of the unmethylated plasmids is governed primarily by Coulombic interactions due to absence of the methyl groups. Use of selected organic modifiers is therefore likely to have only a modest influence on facilitating desorption in these cases.

CONCLUSIONS

Aminoglycoside-derived microbeads (Amikabeads) conjugated with the anticancer drug, doxorubicin, for binding DNA with high efficacy are described herein. The plasmid DNA binding capacity of doxo-beads was higher than that of beads conjugated with berenil, which is a known pseudo-affinity ligand for pDNA binding. Elution of plasmid DNA from drug-conjugated microbeads was enhanced by using organic modifiers in the eluent; acetonitrile was the most efficient among the modifiers evaluated. In general, a higher degree of pDNA elution was seen from doxo-beads indicating significantly better binding and elution performance over berenil-beads. Doxo-beads demonstrated higher binding for pDNA processed using *E. coli* that methylate plasmids compared to those that do not. This selectivity for methylated plasmid over unmethylated plasmids may be useful in diagnostic applications that rely on epigenetic modifications in genomic DNA. Our results indicate that anti-cancer drugs represent a diverse set of ligands that may be exploited for the development of novel DNA binding materials for applications in delivery, diagnostics, and biomanufacturing.

While the preferred embodiments of the present technology have been illustrated in detail, it should be apparent that modifications and adaptations to those embodiments may occur to one skilled in the art without departing from the scope of the present technology. The following claims are not meant to be limited to the embodiments and examples above.

We claim:

1. A composition for selectively binding methylated DNA, comprising a CG-region binding molecule conjugated to a resin, wherein said CG-region binding molecule is conjugated to said resin with a crosslinker, wherein one or more hydroxyl groups of the CG-region binding molecule are modified by moiety consisting of —C(=O)—(CH$_2$)$_n$—R, wherein R is alkyl or aryl and n is 0-3.

2. The composition of claim 1, wherein the resin is aminoglycoside-derived microbeads, having a structure of formula 1:

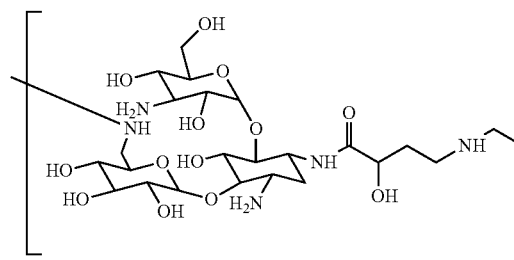 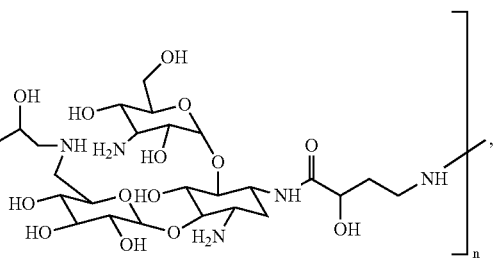

wherein n depends on the average $M_n$ of poly(ethylene glycol) diglycidyl ether.

3. The composition of claim 1, wherein the CG-region binding molecule is selected from the group consisting of Doxorubicin and Epirubicin.

4. The composition of claim 3, wherein the CG-region binding molecule is Doxorubicin.

5. The composition of claim 1, wherein said crosslinker is selected from the group consisting of 1,4-cyclohexane dimethanol diglycidyl ether, neopentylglycol diglycidyl ether, 1,4-butanediol diglycidyl ether, ethylene glycol diglycidyl ether, polypropylene glycol diglycidyl ether, resorcinol diglycidyl ether, glycerol diglycidyl ether, polyethylene glycol diglycidyl ether, polymethyl methacrylate, polyethylene glycol methyl ether, polyethylene glycol diacrylate, polyethylene glycol diamine, Poly(2-hydroxyethyl methacrylate), Poly(D,L-lactide-co-glycolide), poly-lactic acid, polyglycolic acid, Poly[(R)-3-hydroxybutyric acid], Poly(dimethylsiloxane), vinyl terminated, Poly(dimethylsiloxane), and diglycidyl ether.

6. The composition of claim 5, wherein the crosslinker is 1,4-cyclohexane dimethanol diglycidyl ether.

7. The composition of claim 4, wherein one or more hydroxyl groups of doxorubicin are modified with —C(=O)—(CH$_2$)$_n$—R, wherein R is alkyl or aryl and n is 0-3.

8. The composition of claim 2, wherein the aminoglycoside-derived microbeads are generated by injecting amikacin hydrate and poly ethylene glycol diglycidylether (PEGDE) mixture at a mole ratio of 1:2 using emulsion polymerization.

9. The composition of claim 1, wherein the methylated DNA comprises aberrantly hypermethylated CpG islands.

10. A composition for selectively binding methylated DNA, comprising Doxorubicin-conjugated aminoglycoside-derived microbeads, wherein said Doxorubicin is conjugated to said aminoglycoside-derived microbeads with a crosslinker and said aminoglycoside-derived microbeads having a structure of formula 1:

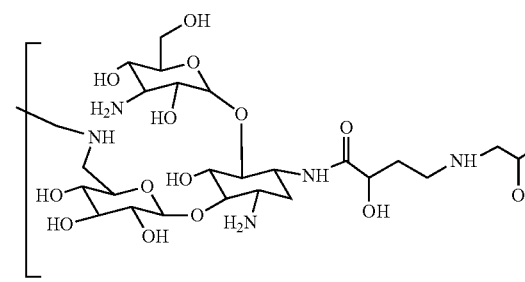 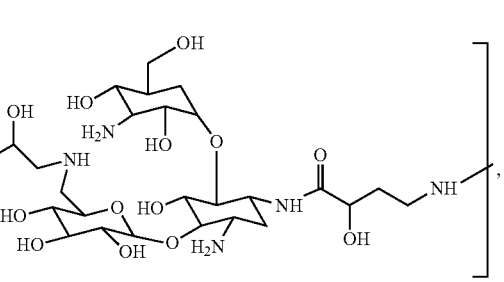

wherein n depends on the average $M_n$ of poly(ethylene glycol) diglycidyl ether and wherein one or more hydroxyl groups of said Doxorubicin are modified by moiety consisting of —C(=O)—(CH$_2$)$_n$—R, wherein R is alkyl or aryl and n is 0-3.

11. The of claim 10, wherein the aminoglycoside-derived microbead are generated by injecting amikacin hydrate and poly ethylene glycol diglycidylether (PEGDE) mixture at a mole ratio of 1:2 using emulsion polymerization.

12. A method for selectively binding methylated DNA, comprising:
contacting a sample containing methylated DNA with a CG-region binding molecule-conjugated resin, wherein said CG-region binding molecule is conjugated to said resin with a crosslinker, wherein one or more hydroxyl groups of the CG-region binding molecule are modified by moiety consisting of —C(=O)—(CH$_2$)$_n$—R, wherein R is alkyl or aryl and n is 0-3.

13. The method of claim 12, wherein the CG-region binding molecule is selected from the group consisting of Doxorubicin and Epirubicin.

14. The method of claim 13, wherein the CG-region binding molecule is Doxorubicin.

15. The method of claim 12, wherein said crosslinker is selected from the group consisting of: 1,4-cyclohexane dimethanol diglycidyl ether, neopentylglycol diglycidyl ether, 1,4-butanediol diglycidyl ether, ethylene glycol diglycidyl ether, polypropylene glycol diglycidyl ether, resorcinol diglycidyl ether, glycerol diglycidyl ether, polyethylene glycol diglycidyl ether, polymethyl methacrylate, polyethylene glycol methyl ether, polyethylene glycol diacrylate, polyethylene glycol diamine, Poly(2-hydroxyethyl methacrylate, Poly(D,L-lactide-co-glycolide), poly-lactic acid, poly-glycolic acid, Poly[(R)-3-hydroxybutyric acid], Poly(dimethylsiloxane), vinyl terminated, Poly(dimethylsiloxane), and diglycidyl ether.

16. The method of claim 15, wherein the crosslinker is 1,4-cyclohexane dimethanol diglycidyl ether.

17. The method of claim 14, wherein one or more hydroxyl groups of doxorubicin are modified with —C(=O)—(CH$_2$)$_n$—R, wherein R is alkyl or aryl and n is 0-3.

18. A method for selectively binding said patient hypermethylated DNA aberrantly from a patient sample, comprising contacting sample containing methylated DNA with a CG-region binding molecule-conjugated resin, wherein said CG-region binding molecule is conjugated to said resin with a crosslinker, wherein one or more hydroxyl groups of the CG-region binding molecule are modified by moiety consisting of —C(=O)—(CH$_2$)$_n$—R, wherein R is alkyl or aryl and n is 0-3.

19. The method of claim 18, wherein said resin comprises aminoglycoside microbeads.

20. The method of claim 18, wherein the CG-region binding molecule is selected from the group consisting of Doxorubicin and Epirubicin.

21. The method of claim 18, wherein said patient sample is selected from the group consisting of urine, blood, sweat, saliva, tears, lymph, cerebrospinal fluid, bone marrow extract, total cells, and patient biopsy cell lysates.

* * * * *